US012702541B2

(12) United States Patent
Toro Estrella et al.

(10) Patent No.: US 12,702,541 B2
(45) Date of Patent: Aug. 11, 2026

(54) BREAST IMPLANTS AND TISSUE EXPANDERS HAVING INTEGRATED SYSTEMS FOR FILLING IMPLANT SHELLS WITH FLUIDS, INFUSING FLUIDS, AND DRAINING FLUIDS FROM BREAST TISSUE SURROUNDING IMPLANT SHELLS

(71) Applicant: Mentor Worldwide LLC, Irvine, CA (US)

(72) Inventors: Hector Toro Estrella, Lake Forest, CA (US); Leo B. Kriksunov, Ithaca, NY (US)

(73) Assignee: Mentor Worldwide LLC, Irvine, CA (US)

( * ) Notice: Subject to any disclaimer, the term of this patent is extended or adjusted under 35 U.S.C. 154(b) by 1086 days.

(21) Appl. No.: 17/846,201

(22) Filed: Jun. 22, 2022

(65) Prior Publication Data

US 2023/0414342 A1 Dec. 28, 2023

(51) Int. Cl.
*A61F 2/12* (2006.01)
*A61B 90/00* (2016.01)

(52) U.S. Cl.
CPC ................ *A61F 2/12* (2013.01); *A61B 90/02* (2016.02); *A61F 2250/0013* (2013.01); *A61F 2250/0067* (2013.01)

(58) Field of Classification Search
CPC ................ A61F 2/12; A61F 2250/0013; A61F 2250/0067; A61F 2250/0003;
(Continued)

(56) References Cited

U.S. PATENT DOCUMENTS

| | | | |
|---|---|---|---|
| 4,429,693 | A | 2/1984 | Blake et al. |
| 4,643,733 | A | 2/1987 | Becker |

(Continued)

FOREIGN PATENT DOCUMENTS

| | | | |
|---|---|---|---|
| WO | 2021/217099 | A1 | 10/2021 |

OTHER PUBLICATIONS

International Search Report and Written Opinion dated Oct. 2, 2023 issued in International Patent Application No. PCT/IB2023/055830.

(Continued)

*Primary Examiner* — Suzette J Gherbi
(74) *Attorney, Agent, or Firm* — TROUTMAN PEPPER LOCKE LLP

(57) ABSTRACT

A breast implant or tissue expander includes an implant shell having an inner chamber and a tube detachably connected with the implant shell. The tube has a first lumen that is in fluid communication with the inner chamber for adding fluid into the inner chamber to increase the size of said implant shell or for removing fluid from the inner chamber to reduce the size of the implant shell. The tube has a second lumen and one or more lateral openings in fluid communication with the second lumen for draining fluid that collects in tissue surrounding the implant shell. The breast implant has a fluid inlet opening formed in the implant shell, and a valve disposed within the fluid inlet opening. The valve is normally biased into a closed position, and is opened by inserting the distal end of the tube into the fluid inlet opening.

17 Claims, 18 Drawing Sheets

(58) Field of Classification Search
CPC ...... A61F 2250/0004; A61F 2250/0059; A61F 2250/006; A61B 90/02
See application file for complete search history.

(56) References Cited

U.S. PATENT DOCUMENTS

| | | | | |
|---|---|---|---|---|
| 4,773,908 | A | 9/1988 | Becker | |
| 4,800,901 | A | 1/1989 | Rosenberg | |
| 4,944,749 | A | 7/1990 | Becker | |
| 5,534,023 | A | 7/1996 | Henley | |
| 8,349,007 | B2 | 1/2013 | Berg et al. | |
| 8,454,690 | B2 | 6/2013 | McClellan | |
| 9,370,414 | B2 * | 6/2016 | Glicksman | A61F 2/12 |
| 9,468,519 | B2 * | 10/2016 | Kronowitz | A61M 39/0208 |
| 10,271,987 | B2 * | 4/2019 | Rajguru | A61F 7/12 |
| 11,185,384 | B2 | 11/2021 | Feinberg et al. | |
| 11,974,943 | B2 * | 5/2024 | Gurskis | A61F 7/0085 |
| 12,023,274 | B2 * | 7/2024 | Gurskis | A61F 7/0085 |
| 12,102,558 | B2 * | 10/2024 | Gurskis | A61F 7/0085 |
| 2008/0177385 | A1 * | 7/2008 | Jahns | A61F 2/0059 623/11.11 |
| 2010/0249946 | A1 * | 9/2010 | Lesh | A61F 2/0059 623/23.72 |
| 2011/0153017 | A1 | 6/2011 | Mcclellan | |
| 2011/0160854 | A1 | 6/2011 | Berg et al. | |
| 2019/0083234 | A1 * | 3/2019 | Sforza | A61M 5/3286 |
| 2019/0117569 | A1 * | 4/2019 | Epps | A61L 31/16 |
| 2019/0133751 | A1 * | 5/2019 | Feinberg | A61F 2/12 |
| 2020/0129258 | A1 * | 4/2020 | Feinberg | A61M 1/60 |
| 2023/0329823 | A1 * | 10/2023 | Toro Estrella | A61B 17/3421 |
| 2023/0346594 | A1 * | 11/2023 | Gurskis | A61F 7/123 |
| 2025/0248814 | A1 * | 8/2025 | Leshecz | A61M 25/1011 |

OTHER PUBLICATIONS

Mentor Saline-Filled & Spectrum Breast Implants, Oct. 2021, 32 pages, Mentor Worldwide LLC, Irving, Texas.

* cited by examiner

BREAST IMPLANTS AND TISSUE EXPANDERS HAVING INTEGRATED SYSTEMS FOR FILLING IMPLANT SHELLS WITH FLUIDS, INFUSING FLUIDS, AND DRAINING FLUIDS FROM BREAST TISSUE SURROUNDING IMPLANT SHELLS

BACKGROUND OF THE INVENTION

Field of the Invention

The present patent application is generally related to implantable devices, and is more specifically related to breast implants and tissue expanders having integrated fluid delivery, drainage, and infusion components.

Description of the Related Art

Implantable prostheses are commonly used to replace or augment body tissue. In the case of the female breast, it is sometimes necessary to remove some or all of the mammary gland and surrounding tissue in order to treat breast cancer. This surgery (e.g., mastectomy) leaves a void that can be filled with an implantable mammary prosthesis that supports surrounding tissue and maintains a normal body appearance. The restoration of a normal body appearance has an extremely beneficial psychological effect on post-operative patients, eliminating much of the shock and depression that often follows extensive surgical procedures. Implantable mammary prostheses are also used for breast enlargement, commonly referred to as breast augmentation.

Following a mastectomy procedure, temporary expansion devices (i.e., tissue expanders) may be utilized for expanding or stretching skin and tissue within the breast area. Tissue expanders are medical devices that are implanted beneath the skin, tissue or muscle of a patient and then gradually inflated with a fluid to stretch the overlying tissue. Tissue expanders are commonly used to either create a pocket for receiving a permanent prosthesis (e.g., a breast implant), or to generate an increased skin surface area in anticipation of the new skin being utilized for grafting or reconstruction.

Tissue expanders are typically formed of a silicone polymer shell. After implantation, a fluid, such as saline, is periodically injected into the tissue expander to enlarge it over time. Between injections, the surrounding skin is permitted to stretch and grow to increase the skin surface area and increase the size of a tissue pocket configured to receive a permanent implant. Typically, a tissue expander has an injection element through which fluid can be introduced into and/or withdrawn from the tissue expander. One type of injection element is an integrated port having a septum that can be pierced with a hypodermic needle for introducing and/or withdrawing fluid from the tissue expander. Alternatively, the injection element may comprise a self-sealing area on the tissue expander, which allows penetration by a hypodermic needle and self-closing after the hypodermic needle has been withdrawn from the tissue expander.

After surgery, surgical drains may be implanted in a patient to prevent blood and lymphatic fluid from building up under the skin, which allows for quicker healing and recovery. Some patients are sent home with the surgical drains implanted and connected to an external reservoir. Emptying the external reservoirs can be traumatic because the patients have to measure and empty the reservoirs periodically (e.g., every morning). Many patients loathe surgical drains and look forward to having the drains removed.

There have been various efforts directed to providing breast implants and tissue expanders. For example, U.S. Pat. No. 4,643,733 to Becker discloses a permanent reconstruction implant including an inflatable flexible prosthesis having an inlet opening, a normally closed valve in the inlet opening, a filling tube having one end detachably connected to the prosthesis at the inlet opening and operable when in the inlet opening to open the valve, and a reservoir connected to the other end of the filling tube. The '733 patent also discloses a method of performing human tissue expansion and providing a permanent reconstruction implant including the steps of providing a permanent prosthesis having an inlet opening, a normally closed valve in the opening, providing a filling tube having one end adapted for insertion into the inlet opening to open the valve and having a self-sealing reservoir at its other end, surgically placing the prosthesis in the area to be expanded and reconstructed and placing the filling tube and reservoir beneath the skin adjacent the prosthesis with the tube one end in the inlet opening, gradually expanding the prosthesis by percutaneous fluid injections into the reservoir, detaching the reservoir and filling tube from the prosthesis, and allowing the prosthesis to remain permanently in position.

U.S. Pat. No. 8,349,007 to Berg et al., the disclosure of which is hereby incorporated by reference herein, discloses a breast implant including an implant shell having an outer surface and defining a first fluid reservoir, and a porous membrane overlying the outer surface of the implant shell and defining a second fluid reservoir. The breast implant includes a filling tube having a first conduit in communication with the first reservoir and a second conduit in communication with the second reservoir. The breast implant includes an injection dome coupled with the filling tube and having a first fluid chamber in communication with the first conduit and a second fluid chamber in communication with the second conduit. The injection dome includes an upper end having an injection cover and a lower end including a support base. The first fluid chamber is located adjacent the injection cover, and the second fluid chamber is located adjacent the support base. A diaphragm divides the first and second fluid chambers from one another.

U.S. Pat. No. 8,454,690 to McClellan discloses tissue expanders having fluid delivery and drainage systems integrated into the tissue expanders. McClellan discloses a tissue expander having a dual remote port that is connected to a first communication channel in communication with the interior of an implant shell of a tissue expander for inflation/deflation of the tissue expander, and a second communication channel in communication with a channel system having a delivery canal for delivery/extraction of fluid to/from the pocket around the tissue expander. The interior of the tissue expander and the channel system are not in fluid communication with one another. The dual remote port is configured to receive fluid from a syringe. A first fluid is delivered through the implant port, and a second fluid is delivered through the pocket port. In some instances, the first fluid may include saline, buffered saline, water, air, or any other fluid that may be provided to the inside cavity of an implant. The second fluid may include medication, antibiotics, anti-microbial solutions, or any other fluid to deliver to the pocket surrounding the tissue expander.

U.S. Pat. No. 11,185,384 to Feinberg et al., the disclosure of which is hereby incorporated by reference herein, discloses a tissue expander having an integrated drain. The tissue expander includes an outer shell having an opening and one or more drainage holes. An injection port is disposed in the opening of the shell and forms a fluid-tight seal with the shell. The injection port includes a needle guard having a needle guard base with a top surface, and a barrier membrane that overlies the top surface of the needle guard base. The barrier membrane defines an inflation chamber located between the top surface of the needle guard base and a bottom surface of the barrier membrane, and a drainage chamber overlying a top surface of the barrier membrane. The tissue expander includes one or more inflation ports that are in fluid communication with the inflation chamber for inflating and deflating the outer shell with a first fluid. A drainage conduit is in fluid communication with and extends between the drainage chamber and the one or more drainage holes for draining a second fluid from outside the shell.

In spite of the above-noted advances, there is a continuing need for improved breast implants and tissue expanders having integrated components that may be used for both inflating and deflating the breast implants and tissue expanders, draining fluid (e.g., seroma) that collects around the breast implants and tissue expanders following surgery, and infusing fluid (e.g., an antibiotic solution) around the outside of implanted breast implants and tissue expanders. Moreover, there remains a need for breast implants and tissue expanders that provide for the removal of seroma fluid without the need for a drain being continuously attached to a patient for 24 hours a day.

SUMMARY OF THE INVENTION

In the present patent application, the terms breast implant and tissue expander may be used interchangeably.

In one embodiment, a breast implant or tissue expander preferably includes an implant shell (e.g., an elastomeric shell made of silicone) having an inner chamber and a tube having a proximal end and a distal end, whereby the distal end of the tube is detachably connected with the implant shell. In some embodiments, the inventive implant or tissue expander shell is at least partially filled with saline or a similar water-based filling liquid. In some embodiments, the shell is partially filled with silicone gel, and partially filled with saline or a similar liquid. In some embodiments, the inventive breast implant is a permanently installed, saline-filled implant configured for size/volume adjustments by supplying extra saline or withdrawing extra saline through the tube. In some embodiments, the inventive tissue expander is configured for temporary installation into the body for expanding a tissue pocket over a period of several days, several weeks or several months, by infusing extra saline over time though the tube. The inventive tissue expander is further configured for removal from the body or from the tissue pocket after the expansion, and to be replaced by a permanent implant, which may be a saline filled or silicone gel filled implant.

In one embodiment, the tube has a first lumen that extends between the proximal and distal ends thereof. in one embodiment, the first lumen is in fluid communication with the inner chamber for adding fluid (e.g., saline) into the inner chamber to increase the size of the implant shell and/or for removing fluid from the inner chamber to reduce the size of the implant shell.

In one embodiment, the tube has a second lumen and one or more lateral openings formed in an outer wall of the tube that are in fluid communication with the second lumen for draining fluid that collects is tissue (e.g., a pocket formed in breast tissue) surrounding an outer perimeter of the implant shell.

In one embodiment, the breast implant includes a fluid inlet opening formed in the implant shell, and a valve disposed within the fluid inlet opening. The valve is normally biased into a closed position for preventing fluid disposed within the inner chamber of the implant shell from leaking from the breast implant.

In one embodiment, the distal end of the tube is detachably connected with the implant shell via the fluid inlet opening. In one embodiment, when the distal end of the tube is inserted into the fluid inlet opening, the distal end of the tube preferably engages the valve for moving the valve into an open position so that fluid may be added into the shell or removed from the shell.

In one embodiment, the tube may be a dual-lumen tube including the first and second lumens extending between the proximal and distal ends of the dual-lumen tube.

In one embodiment, the one or more lateral openings that are in fluid communication with the second lumen preferably include a series of laterally extending openings (e.g., slits) that are spaced from one another, that extend along the length of the tube, and that are located adjacent the distal end of the tube.

In one embodiment, the tube defines a first length and the series of laterally extending openings define a second length that is less than 90% of the first length. In one embodiment, the series of laterally extending openings may extend adjacent the distal end of the tube.

In one embodiment, a tube with laterally extending openings may be wrapped completely around an outer perimeter of a shell for draining fluid that accumulates around the outer perimeter of the shell.

In one embodiment, a fill port may be coupled with a proximal end of the first lumen. The fill port is configured for adding fluid into the inner chamber of the implant shell to increase the size of the breast implant. The fill port may also be used to remove fluid from the implant shell to reduce the size of the breast implant.

In one embodiment, a drainage port may be coupled with a proximal end of the second lumen. The drainage port is configured for draining fluid (e.g., seroma) from the tissue surrounding the outer perimeter the implant shell. After surgery, the fluid may accumulate around the outside of the implant shell and draining the fluid will desirably promote healing and recovery for the patient.

In one embodiment, the tube may include a third lumen that extends along the length of the tube for infusing a therapeutic fluid (e.g., an antibiotic solution) into the tissue (e.g., breast tissue) surrounding the outer perimeter of the implant shell.

In one embodiment, the third lumen may be utilized for infusing fluid around the implanted shell, and the second lumen may be used for draining the fluid from around the shell, thereby providing medical personnel with a system for flushing the breast tissue that surrounds the breast implant or tissue expander.

In one embodiment, one or more infusion openings may be formed in the tube, the one or more infusion openings being in fluid communication with the third lumen. In one embodiment, the one or more infusion openings are formed in an outer wall of the tube. The one or more infusion openings are preferably configured for infusing a therapeutic fluid into the tissue that surrounds the outer perimeter of the implant shell. The therapeutic fluid that flows through the third lumen preferably passes through the one or more infusion openings for bathing the breast tissue with the therapeutic fluid.

In one embodiment, the one or more infusion openings are located adjacent the distal end of the tube. In one embodiment, the one or more infusion openings comprise a series of infusion openings having a length that is less than 90% of the length of the tube, and more preferably less than 50% of the length of the tube.

In one embodiment, a breast implant or tissue expander may include an elastomeric shell having an inner chamber, and a tube having a proximal end and a distal end.

The breast implant or tissue expander may be implanted within a pocket formed in breast tissue.

In one embodiment, the tube preferably includes a first lumen that is in fluid communication with the inner chamber for filling the inner chamber with a fluid for expanding the elastomeric shell.

In one embodiment, the tube preferably includes a second lumen and one or more lateral openings in fluid communication with the second lumen for draining fluid from tissue surrounding an outer perimeter of the shell.

In one embodiment, the breast implant may include a fluid inlet opening formed in the elastomeric implant shell, and a valve disposed within the fluid inlet opening that is normally biased in a closed position.

In one embodiment, the distal end of the tube is detachably connected with the implant shell via the fluid inlet opening.

In one embodiment, when the distal end of the tube is inserted into the fluid inlet opening, the distal end of the tube forces the valve to move into an open position.

In one embodiment, when the distal end of the tube is detached from the fluid inlet opening, the distal end of the tube disengages from the valve for enabling the valve to return to the normally closed position.

In one embodiment, a third lumen extends along the length of the tube for infusing a therapeutic fluid into the tissue surrounding the outer perimeter of the elastomeric shell.

In one embodiment, a series of laterally extending infusion openings are formed in the tube that are in fluid communication with the third lumen. The series of laterally extending infusion openings are configured for infusing the therapeutic fluid into the tissue surrounding the outer perimeter of the elastomeric shell.

In one embodiment, a breast implant preferably includes an implant shell having an inner chamber, and a three lumen tube having a proximal end and a distal end, whereby the distal end of the three lumen tube is detachably connected with the implant shell.

In one embodiment, the three lumen tube preferably includes a first lumen that extends between the proximal and distal ends thereof.

In one embodiment, the first lumen is in fluid communication with the inner chamber for adding fluid into the inner chamber to increase the size of the breast implant and/or for removing fluid from the inner chamber to reduce the size of the breast implant.

In one embodiment, the three lumen tube desirably includes a second lumen and one or more laterally extending drainage openings that are in fluid communication with the second lumen for draining fluid that collects in the tissue surrounding an outer perimeter of the implant shell.

In one embodiment, the three lumen tube preferably includes a third lumen and one or more laterally extending infusion openings that are in fluid communication with the third lumen for infusing fluid into the tissue surrounding the outer perimeter of the implant shell.

In one embodiment, the breast implant may include a fluid inlet opening formed in the implant shell, and a valve disposed within the fluid inlet opening.

In one embodiment, the valve is normally biased in a closed position.

In one embodiment, when the distal end of the tube is inserted into the fluid inlet opening, the valve is forced into the open position and the first lumen of the tube is in fluid communication with the fluid inlet opening and the inner chamber for filling the inner chamber with a fluid for expanding the size of the implant shell.

In one embodiment, the distal end of the tube is detachably connected with the implant shell via the fluid inlet opening. In one embodiment, when the distal end of the tube is detached from the fluid inlet opening, the valve, which is no longer engaged by the distal end of the tube, returns to the closed position for sealing the fluid inlet opening and preventing fluid leaks from the shell.

In one embodiment, a fill port may be coupled with a proximal end of the first lumen. The fill port is configured for adding fluid into the inner chamber of the implant shell to increase the size of the implant shell. The fill pot may also be used for removing fluid from the implant shell to reduce the size of the implant shell.

The fill port may be implanted beneath a patient's skin.

In one embodiment, a drainage port may be coupled with a proximal end of the second lumen to drain fluid from the tissue surrounding the outer perimeter the implant shell.

The drainage port may be implanted beneath a patient's skin.

In one embodiment, an infusion port may be coupled with a proximal end of the third lumen to infuse fluid into the tissue surrounding the outer perimeter the implant shell.

In one embodiment, the infusion port may be implanted beneath a patient's skin.

In one embodiment, a separate port is removably attached to the proximal ends of each of the respective first and second lumens.

In one embodiment, when the elastomeric shell is implanted, the one or more laterally extending openings may be in fluid communication with surrounding tissue (e.g., the tissue that defines a breast pocket).

In one embodiment, the one or more laterally extending openings may be used to irrigate tissue and/or to remove fluids that accumulate within the breast pocket that surrounds the implant.

In one embodiment, the adjustable breast implant has two lumens, a first lumen for filling the shell with a liquid (e.g., saline), and a second lumen with one or more side openings (e.g., slits) that are used to drain fluids (e.g., seroma) from a breast pocket that surrounds the implant.

In one embodiment, the one or more side openings may be used to introduce therapeutics that promote healing or minimize the likelihood of infection.

In one embodiment, a first port may be attached to a single lumen tube to add fluid to the shell with a needle or luer connection.

In one embodiment, a second port may be attached to a single lumen to remove fluid from the breast pocket with a needle or luer connection.

In one embodiment, a dual-lumen tube may be positioned (e.g., intraoperatively) strategically within an area where a surgeon desires to remove fluid from a breast pocket (e.g., closer to the inframammary fold, axilla, or upper pole, etc.).

In one embodiment, the ports that are used to fill and/or drain bodily fluids from the shell may be positioned (e.g., intraoperatively) in locations where a surgeon desires to access the tubes for filling or draining.

In one embodiment, when size adjusting and draining activities are complete, the dual-lumen tube and/or two single lumen tubes with respective ports may be removed from the shell in a manner that is similar to that used for the breast implant sold under the trademark SPECTRUM breast implant by Mentor Worldwide LLC of Irvine, California.

In one embodiment, a drain tube may be used to access a breast pocket to irrigate and/or add fluid medication into the breast pocket that surrounds a shell of a breast implant.

In one embodiment, the implant shell is adapted to expand upon introducing a saline solution into the first reservoir. The implant shell may be filled with saline solution.

In one embodiment, the filling tube preferably has a distal end and a proximal end, whereby the distal end of the filling tube is coupled with the implant shell and the proximal end of the implant shell is coupled with an injection dome. The filling tube may be a dual-lumen filling tube. The distal end of the filling tube may be releasably coupled with the implant shell.

In one embodiment, it may be desirable to infuse a fluid, such as saline or an antibiotic or drug solution, into a breast pocket that surrounds the implant shell.

In one embodiment, the implant shell, in an at least partially collapsed state, may be inserted into a pocket formed in breast tissue, The tube (e.g., a two lumen tube) preferably extends outside the patients body so that a proximal end of the tube may be coupled with a fluid filled syringe. A plunger on a syringe may be depressed for introducing a first fluid (e.g., saline) into the inner chamber of the shell of the implant. A second fluid, such as a drug solution, may be infused around the outside of the implant shell. After the surgeon is satisfied that the implant has been expanded to a sufficient size, or after the surgeon is satisfied that sufficient drug solution has been introduced, the syringe is preferably de-coupled from the proximal end of the tube.

In one embodiment, after the surgeon or medical personnel are satisfied that no further fluids need to be introduced into and/or removed from the implant shell, the surgeon or medical personnel may de-couple the distal end of the tube (e.g., a filling tube) from the expandable implant. In one embodiment, a forceps-like tool may be utilized for tugging on a section of the tube that is accessible outside the patients body. As soon as the tube is de-coupled from the implant, one or more valves interconnecting the tube with the implant automatically close for sealing the implant and preventing leaks.

In one embodiment, the proximal end of the filling tube preferably extends outside the patient's body so that the injection dome may be accessible outside the body.

In one embodiment, the entire length of the filling tube and the injection dome are positioned below a patient's skin surface (e.g., implanted beneath the patient's skin). Additional fluid may be introduced into and/or removed from the injection dome by advancing an injection needle through the patient's skin for engaging the injection dome.

These and other preferred embodiments of the present patent application will be described in more detail herein.

BRIEF DESCRIPTION OF THE DRAWINGS

FIG. 2A-1 is a cross-sectional view of the dual-lumen tube shown in FIG. 2A.

FIG. 9A-1 is a cross-sectional view of the triple-lumen tube shown in FIG. 9A.

DETAILED DESCRIPTION OF PREFERRED EMBODIMENTS

Figure 1A:
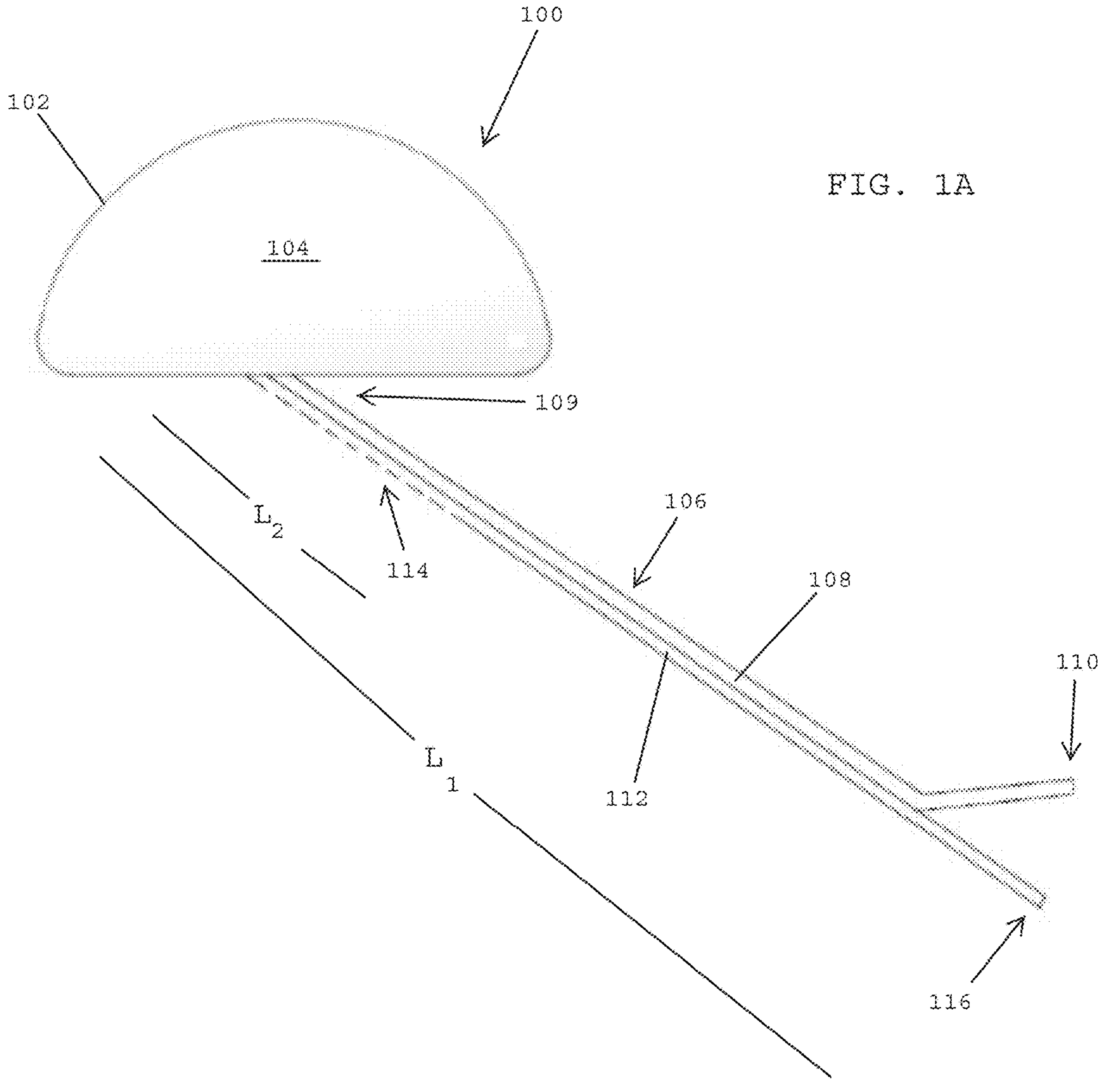
FIG. 1A is a schematic view of a breast implant including a shell and a dual-lumen tube having a first lumen for filling the shell with a fluid and a second lumen in communication with lateral openings formed in an outer wall of the dual-lumen tube for draining fluid that accumulates around the shell, in accordance with one embodiment of the present patent application.
Figure 1B:
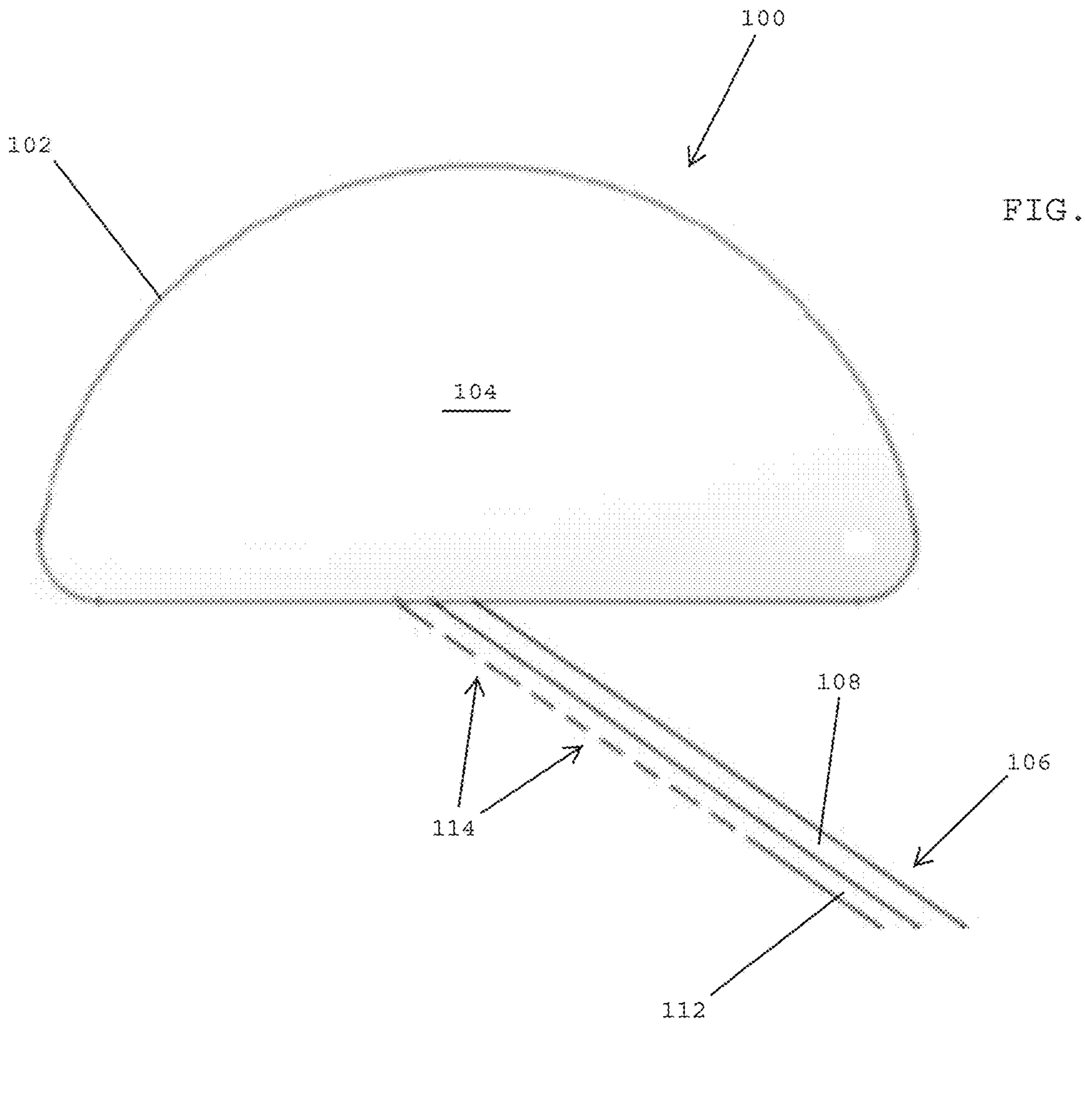
FIG. 1B is a magnified view of the shell and a distal end of the dual-lumen tube shown in FIG. 1A.

Referring to FIGS. 1A and 1B, in one embodiment, a breast implant 100 (also referred to herein as a "tissue expander") preferably includes a shell 102 that defines an inner chamber 104, which is configured for being filled with a fluid (e.g., saline) for expanding the size of the shell.

In one embodiment., the shell 102 may have any desired shape and any thickness that is suitable for the purpose of the particular tissue expander. The shell 102 may be formed of a biocompatible elastomeric material such as silicone.

In one embodiment, an appropriately sized and shaped mandrel may be used to form the shell 102 of the tissue expander 100. In one embodiment, the shell 102 may be formed using a dip molding methodology, although other methodologies may be used including spraying a mandrel with a shell forming solution or using an injection molding process. During one preferred dip molding method, a mandrel is dipped into a silicone dispersion and then removed to allow for partial curing and solvent evaporation. The dipping step may be repeated several times. Once the shell has been formed, it may be removed from the mandrel. The dip molding process may result in the formation of a partial shell that has an opening (e.g., a circular hole; a patch hole). An injection port, a valve, and/or a safety patch may be installed in the opening, thus forming a complete, fluid impervious shell.

In one embodiment, the completed shell can be non-filled or partially pre-filled. After implantation into a breast pocket, the breast implant 100 may be filled with saline, gel, foam, and/or combinations of these materials or other suitable materials known in the art to gradually expand the size of the shell 102 to the desired dimensions. Expansion of the breast implant may occur gradually and take place over the course of several office visits.

In one embodiment, the breast implant 100 preferably includes a tube 106 (e.g., a dual-lumen tube) having a first lumen 108 that is utilized for filling the inner chamber 104 of the shell 102 with a fluid. In one embodiment, the first lumen 108 has a proximal end 110 that is configured for being coupled with a fill port, which may be utilized for introducing a fluid into the first lumen 108.

In one embodiment, the first lumen 108 of the dual-lumen tube 106 may be used for adding fluid to the inner chamber 104 to expand the size of the shell 102 and/or to remove fluid from the inner chamber to reduce the size of the shell.

In one embodiment, the dual-lumen tube 106 preferably includes a second lumen 112 and one or more lateral openings 114 in fluid communication with the second lumen for draining fluid that accumulates around an outer perimeter of the shell 102 of the breast implant 100. In one embodiment, a vacuum may be generated within the second lumen, which, in turn, draws accumulated fluids through the one or more lateral openings and into the second lumen for being drained from a patient's body.

In one embodiment, the one or more lateral openings 114 preferably define a series of openings that are located adjacent a distal end 109 of the dual-lumen tube 106. In one embodiment, the second lumen 112 has a proximal end 116 that is configured for being coupled with a drain port for draining the fluid that is drawn through the one or lateral openings 114 and into the second lumen 112.

In one embodiment, the dual-lumen tube 106 desirably has a first length $L_1$ and the one or more lateral openings 114 define a series of lateral openings having a second length $L_2$ that is less than the first length $L_1$. In one embodiment, the series of lateral openings 114 located at the distal end 109 of the dual-lumen tube extend approximately $\frac{1}{3}^{rd}$ of the first length $L_1$ of the dual-lumen tube 106, adjacent the distal end 109 of the dual-lumen tube 106. In one embodiment, the series of lateral openings may extend about 90% of the total length of the tube.

Referring to FIG. 1B, in one embodiment, the series of lateral openings 114 formed in the dual-lumen tube 106 are preferably in communication with the second lumen 112. In one embodiment, after the shell has been implanted within a patient, fluid (e.g., seroma) may accumulate within a breast pocket that surrounds the shell 102 of the breast implant 100. A medical device (e.g., a syringe; a drainage system) may be coupled with the proximal end 116 (FIG. 1A) of the second lumen 112 of the dual-lumen tube 106 for being in communication with the second lumen 112 for suctioning the fluid through the series of lateral openings 114 formed in a sidewall of the tube 106, whereupon the suctioned fluid may be drained from the patient's body via the second lumen 112.

Figure 2A:
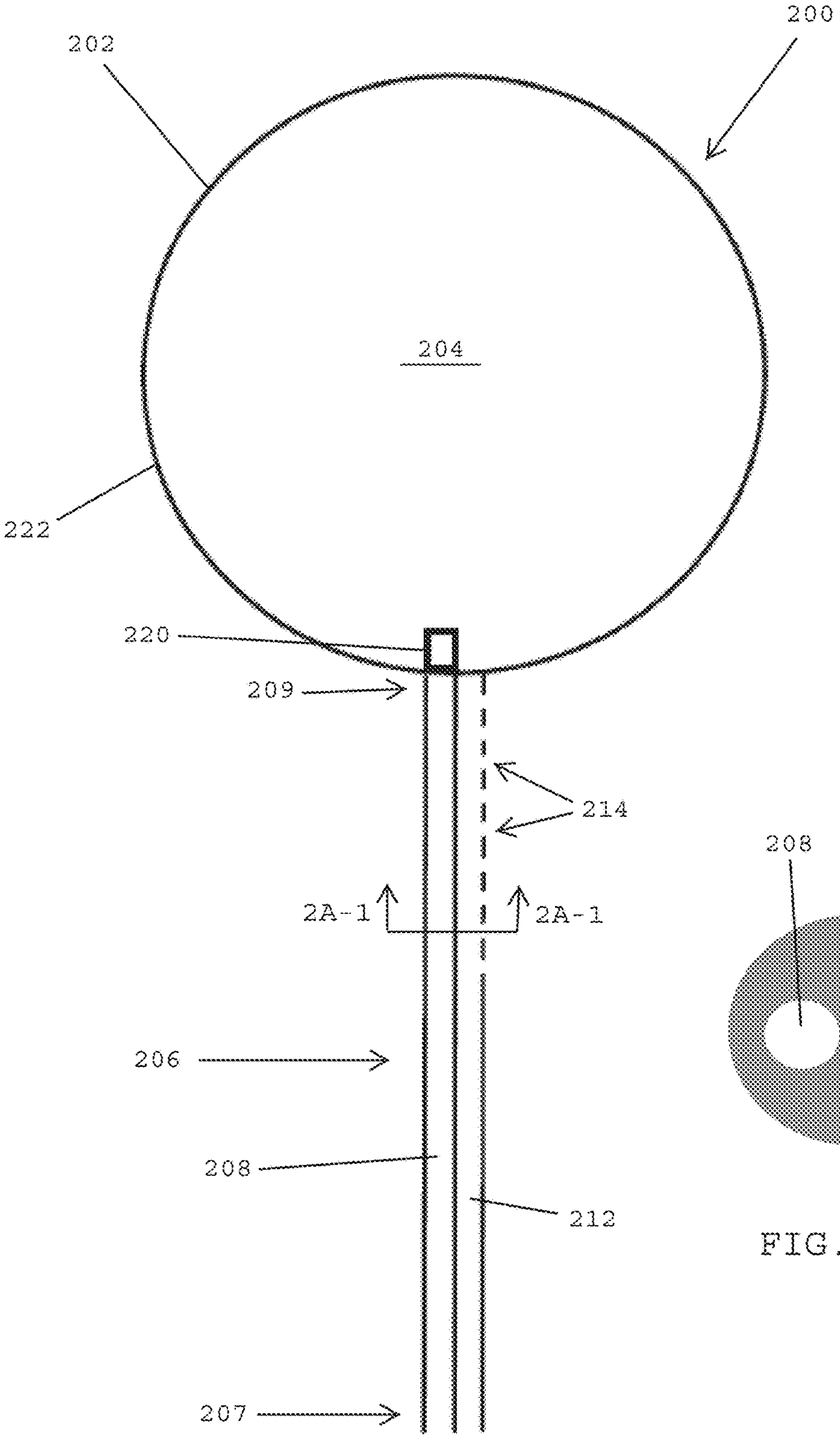
FIG. 2A is a schematic view of a breast implant including a shell and a dual-lumen tube having a first lumen for filling the shell with a fluid and a second lumen for draining fluid that accumulates around the perimeter of the shell, in accordance with one embodiment of the present patent application.
Figures 1, 2A:
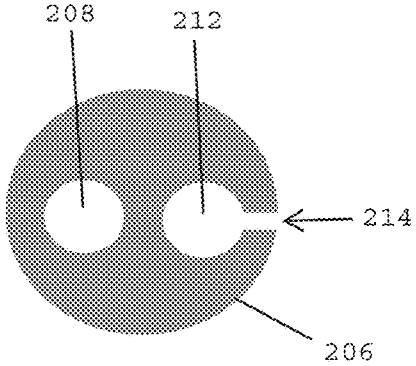
Figure 2B:
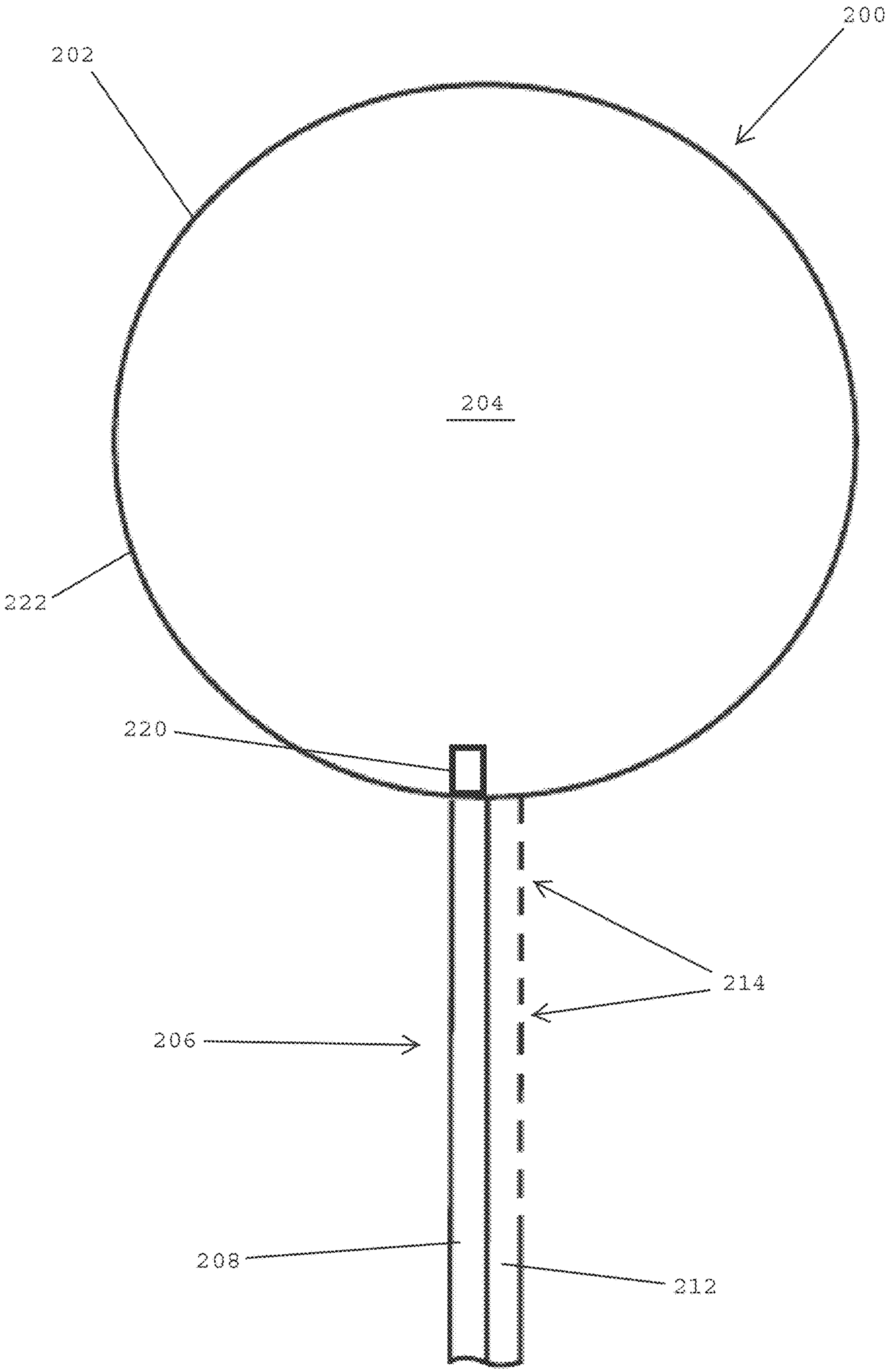
FIG. 2B is a magnified view of the shell and a distal end of the dual-lumen tube shown in FIG. 2A.

Referring to FIGS. 2A and 2B, in one embodiment, a breast implant 200 preferably includes a shell 202 that defines an inner chamber 204 that is configured for being filled with a fluid, such as saline.

In one embodiment, the breast implant 200 preferably includes a dual-lumen tube 206 having a proximal end 207 and a distal end 209 that is coupled with the shell 202. The distal end 209 of the tube 206 may be inserted into an opening in the shell that is used for filling the shell with a fluid (e.g., saline).

In one embodiment, the dual-lumen tube 206 preferably includes a first lumen 208 that extends between the proximal end 207 and the distal end 209 of the dual-lumen tube 206. The first lumen 208 is preferably configured for introducing a fluid, such as saline, into the inner chamber 204 of the shell 202 for expanding the size of the shell. The first lumen 208 may also be used for removing fluid from the inner chamber 204 of the shell 202 for reducing the size of the shell.

In one embodiment, the dual-lumen tube 206 preferably includes a second lumen 212 that is configured for draining fluid (e.g., seroma; bodily fluids) that accumulates around an outer perimeter of the shell 202. In one embodiment, the dual-lumen tube 206 preferably includes a series of lateral openings 214 formed therein that are in fluid communication with the second lumen 212 for enabling bodily fluids that accumulate around the shell 202 to be drawn into the second lumen 212 for being removed from the patient's body. In one embodiment, the series of lateral openings 214 that are in fluid communication with the second lumen 212 are desirably implanted inside the patient so that the openings 214 are not exposed to ambient air, which prevents the ambient air from being sucked into the second lumen as fluid is being drained from around the shell of the breast implant. In one embodiment, the series of lateral openings 214 for draining fluid from around the implant may extend up to 90% or more of the total length of the dual-lumen tube 206. In one embodiment, the series of lateral openings 214 are preferably located adjacent the distal end 209 of the dual-lumen tube 206. In one embodiment, the series of lateral openings 214, located adjacent the distal end of the dual-lumen tube, may extend approximately one-third ($1/3^{rd}$) of the total length of the dual-lumen tube 206.

Referring to FIG. 2A-1, in one embodiment, the dual-lumen tube 206 preferably includes the first lumen 208 that is utilized for filling the inner chamber 204 of the shell 202 (FIG. 2A) with a fluid (e.g., saline), and a second lumen 212 that includes the series of lateral openings 214, which are utilized for draining fluid that accumulates around the outer perimeter of the shell 202 (FIG. 2A).

Referring to FIGS. 2A and 2B, in one embodiment, the breast implant 200 preferably includes a valve 220 that is secured to an inner surface of a wall 222 of the shell 202. In one embodiment, the valve 220 preferably projects into the inner chamber 204 of the shell 202. As will be described in more detail herein, the valve 220 is preferably adapted to receive the distal end 209 of the dual-lumen tube 206 for forming a fluid-tight seal between the first lumen 208 of the dual-lumen tube 206 and the outer wall 222 of the shell 202 to prevent fluid leakage as the fluid is introduced into the interior chamber 204 of the shell 202. In one embodiment, when the distal end of the dual-lumen tube is uncoupled from the valve 220, the valve is configured to close and/or seal to prevent the fluid disposed within the inner chamber 204 of the shell 202 from leaking from the shell 202 of the breast implant 200.

In one embodiment, the valves disclosed in the present patent application may be similar to and/or incorporate one or more components of the valves disclosed in U.S. Pat. Nos. 4,643,733; 4,773,908; and 4,944,749 to Hilton Becker, the disclosures of which are hereby incorporated by reference herein.

In one embodiment, a breast implant or tissue expander disclosed herein may incorporate one or more of the systems or components disclosed in U.S. Pat. Nos. 8,349,007 and 11,185,384, assigned to Mentor Worldwide LLC of Irvine, California, the disclosures of which are hereby incorporated by reference herein.

Figure 3:
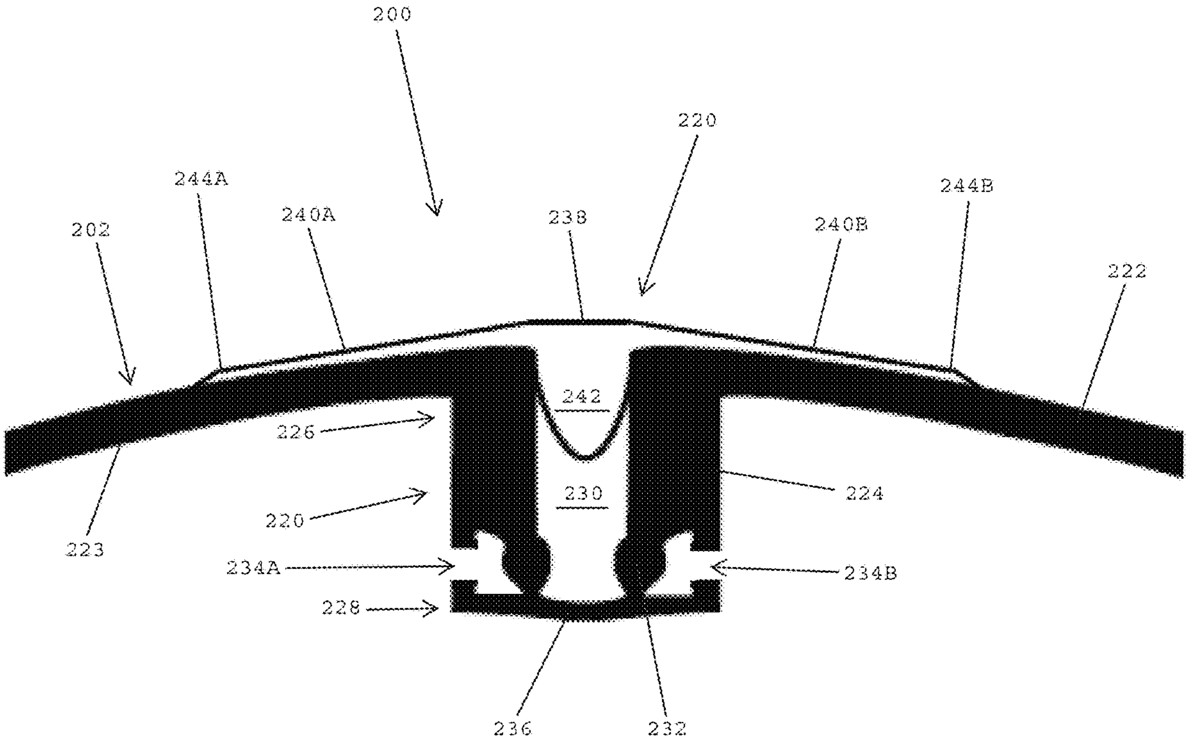
FIG. 3 is a cross-sectional view of a section of a section of a shell of a breast implant with a valve projecting inwardly from an outer wall of the shell, in accordance with one embodiment of the present patent application.

Referring to FIG. 3, in one embodiment, the breast implant 200 shown in FIGS. 2A and 2B preferably includes the valve 220 that projects inwardly from an inner surface 223 of the wall 222 of the shell 202. In one embodiment, the valve 220 preferably includes a valve tube 224 having a proximal end 226 that is secured to the wall 222 of the shell 202 and a distal end 228 that is disposed within the inner chamber 204 of the shell 202.

In one embodiment, the valve 220 desirably includes a central opening 230 that extends along the length of the valve tube 224 from the proximal end 226 of the distal end 228 thereof. In one embodiment, the central opening 230 may be used for filling the shell with a fluid and/or removing a fluid from the shell. In one embodiment, the valve tube 224 preferably includes a sealing ring 232 that projects from the distal end thereof.

In one embodiment, the valve 220 preferably includes first and second lateral openings 234A, 234B that are formed in the outer wall of the valve tube 224. In one embodiment, when the valve 220 is opened, the first and second lateral openings 234A, 234B are preferably in fluid communication with the central opening 230 of the valve 220.

In one embodiment, the valve 220 desirably includes a flexible diaphragm 236 that normally engages the distal end of the sealing ring 232 for closing the valve 202 and preventing fluid from leaking via the central opening 230 of the valve 220. As will be described in more detail herein, under positive pressure, the flexible diaphragm 236 may be forced away from the distal end of the sealing ring 232 to form a gap between the flexible diaphragm and the sealing ring, which provides fluid communication between the first and second lateral openings 234A, 234B and the central opening 230 of the valve tube 224.

In one embodiment, the valve 220 preferably includes a valve plug 238 that may be inserted into the central opening 230 of the valve tube 224 for plugging the central opening 230 and preventing fluid from leaking from the inner chamber 204 of the shell 202 of the breast implant 200. In one embodiment, the valve plug 238 preferably includes first and second flexible straps 240A, 240B having respective inner ends that are connected with a plug body 242 and respective outer ends that are secured to the outer surface of the wall 222 of the shell 202 via anchor points 244A, 244B.

Figure 4:
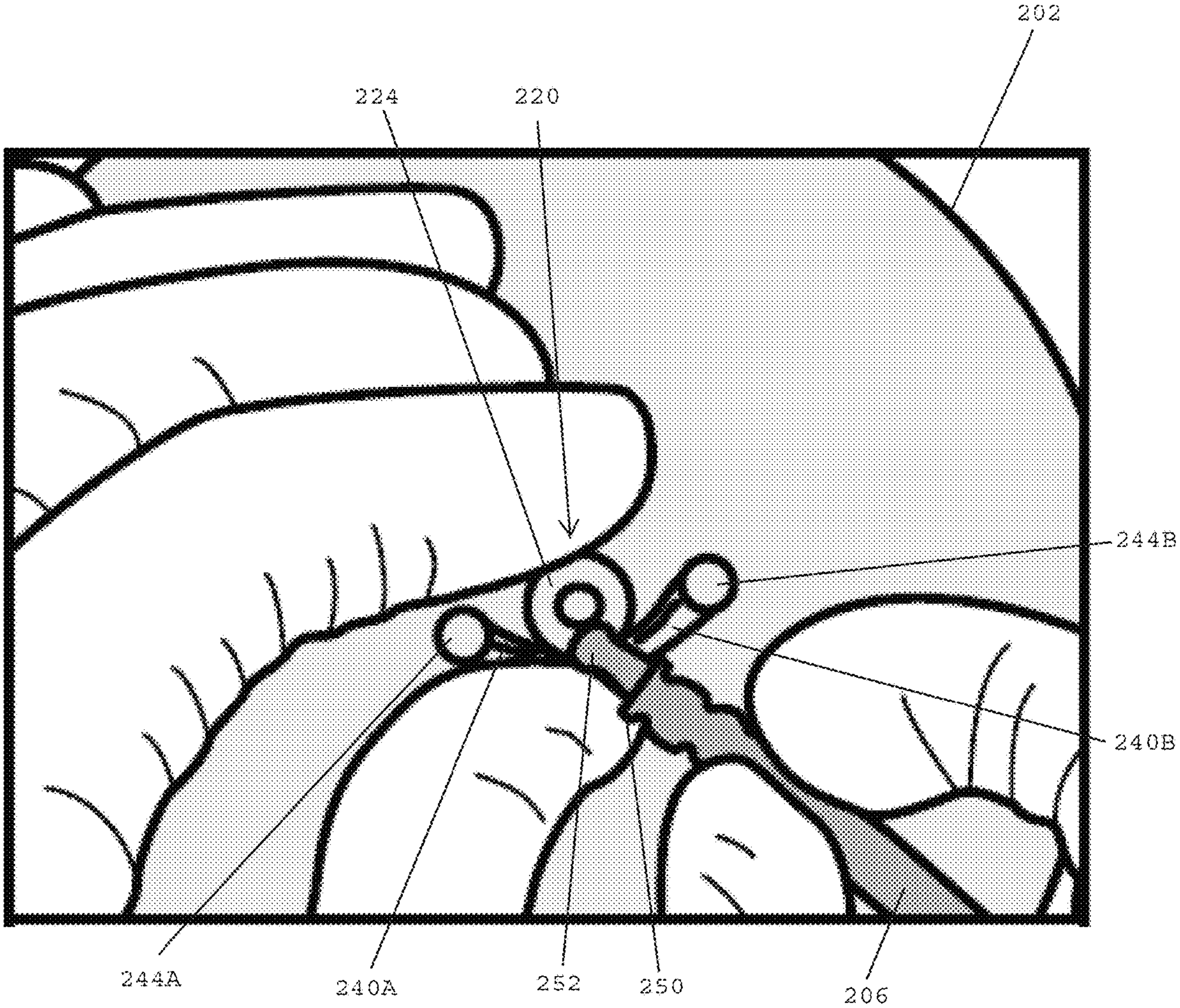
FIG. 4 shows a method of inserting a distal end of a tube into the valve of FIG. 3 for filling the shell with a fluid, in accordance with one embodiment of the present patent application.

Referring to FIG. 4, in one embodiment, a distal end of the dual-lumen lumen 206 preferably includes a shoulder 250 and a bulb 252 that projects distally from the shoulder 250. In one embodiment, in order to couple the distal end of the dual-lumen tube 206 with the valve 220 (e.g., for filing the shell with saline), the plug mass 242 (FIG. 3) of the valve plug 238 may be pulled away from the central opening 230 of the valve tube 224 to provide access to the central opening 230 of the valve 220. As the valve plug is pulled away from the central opening 230 of the valve 220, the first and second flexible straps 240A, 240B preferably stretch. With the central opening 230 of the valve 220 exposed, the bulb-shaped distal end 252 of the tube 206 may be inserted into the central opening 230 of the valve 220 for opening the valve.

Figure 5:
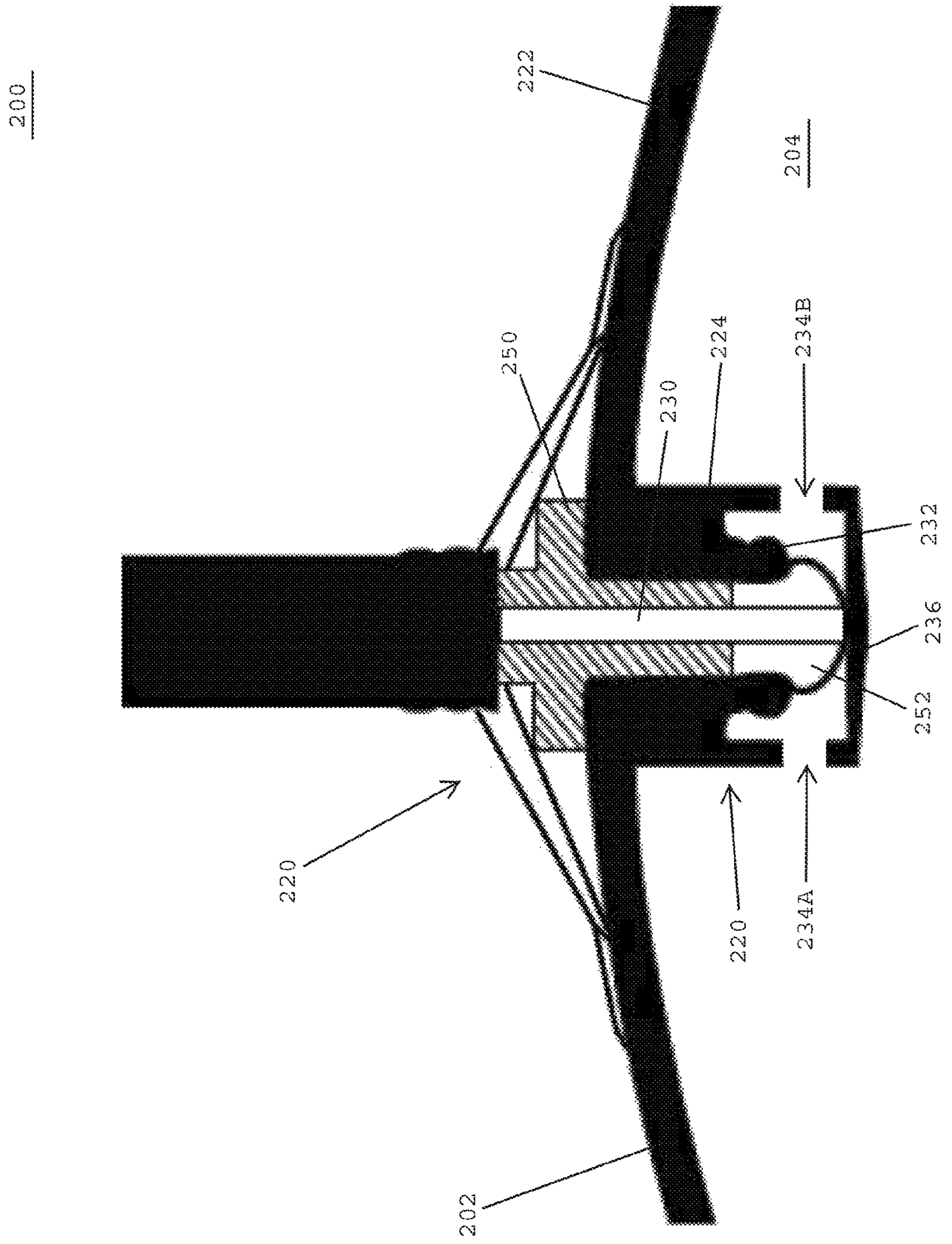
FIG. 5 shows the distal end of the tube of FIG. 4 after being inserted into the valve shown in FIG. 3 for filling the shell with a fluid, in accordance with one embodiment of the present patent application.

Referring to FIG. 5, in one embodiment, the bulb-shaped distal end 252 of the tube 206 may be inserted into the central opening 230 (FIG. 4) of the valve 220 until the shoulder 250 located proximal to the bulb-shaped distal end 252 abuts against an outer surface of the wall 222 of the shell 202. In the position shown in FIG. 5, the bulb-shaped distal end 252 of the tube 206 forces the diaphragm 236 to move away from the distal end of the sealing ring 232 of the valve tube 224 to open the valve and provide fluid communication between the central opening 230 of the valve tube 224 and the first and second lateral openings 234A, 234B formed in the outer wall of the valve tube 224. With the flexible diaphragm 236 flexed into the position shown in FIG. 5, a fluid may be passed in series through the first lumen of the tube 206, the central opening 230 of the valve 220, and through the respective first and second lateral openings 234A, 234B for filling the inner chamber 204 of the shell 202 of the breast implant 200.

Figure 6:
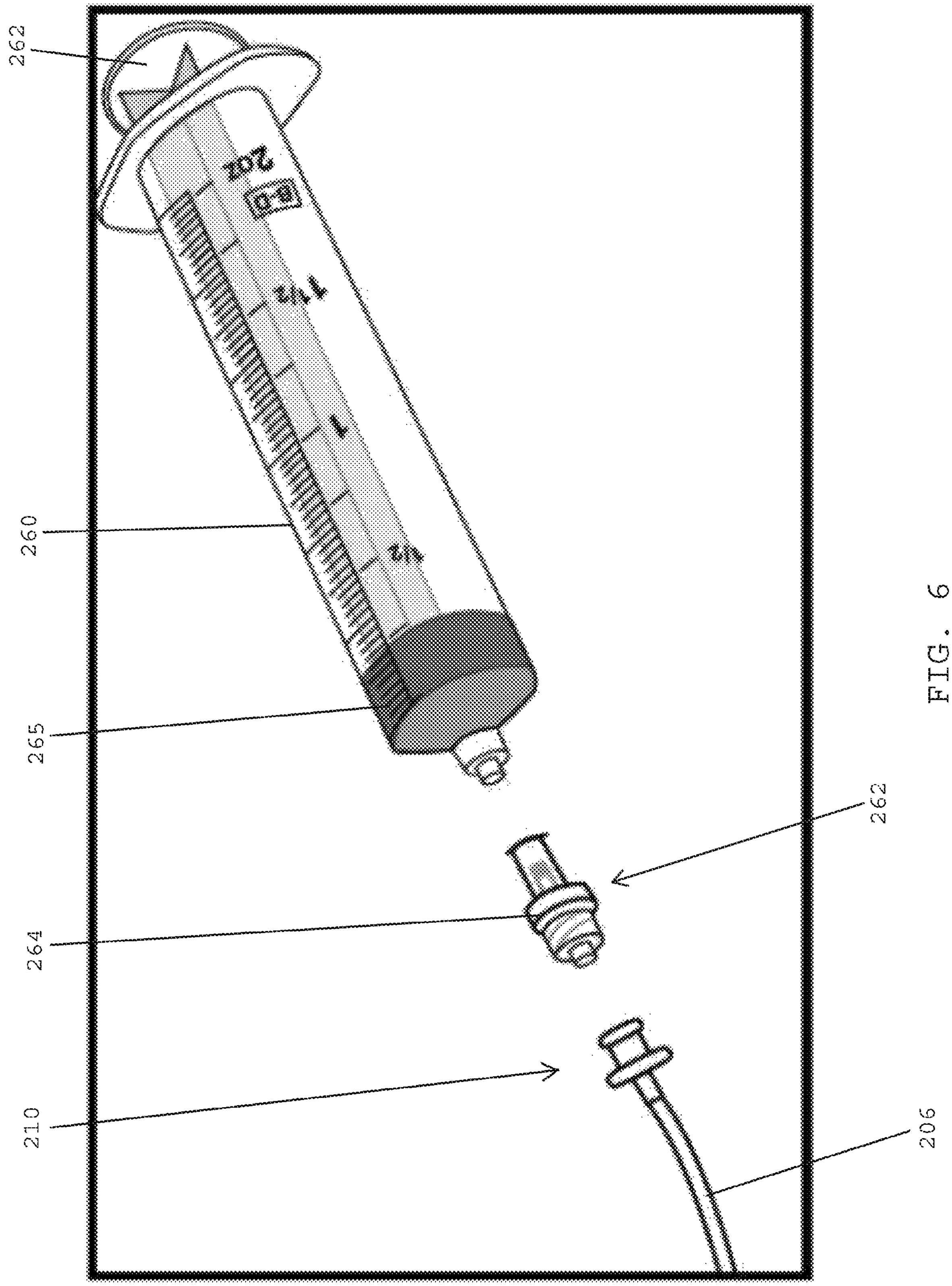
FIG. 6 illustrates a method of coupling a fluid-filled syringe with a proximal end of a tube for filling a shell of a breast implant with a fluid, in accordance with one embodiment of the present patent application.

Referring to FIG. 6, in one embodiment, a syringe 260 may be utilized for filling the inner chamber 204 of the shell 202 of the breast implant 200 (FIG. 5) with a fluid such as saline or a drug solution. The syringe 260 preferably contains a fluid 265 (e.g., saline). In one embodiment, a proximal end 210 of the tube 206 may be coupled with a distal end of the syringe 260 using a luer adapter 262 and a two-way check valve 264. After the syringe 260 is coupled with the proximal end 210 of the tube 206, a plunger 266 on the syringe 260 may be depressed for forcing the fluid 265 to flow through the tube 206, through the open valve 220 (FIG. 5) and into the inner chamber of the shell of the breast implant. If necessary, the plunger 266 may be retracted relative to the distal end of the syringe 260 for removing fluid and/or solution from the shell of the breast implant. The arrangement shown in FIG. 6 is preferably used during a surgical procedure when a breast implant is initially disposed within a tissue pocket and filled with a fluid and/or solution for expanding the size of the breast implant.

Figure 7:
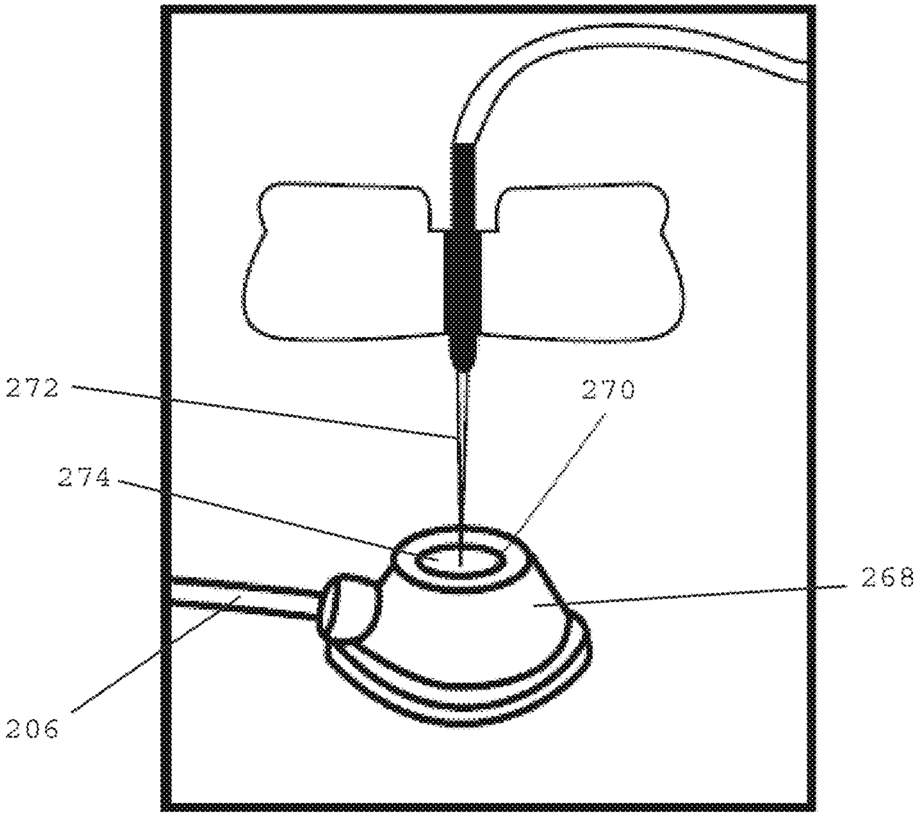
FIG. 7 shows a method of using an injection needle for dispensing a fluid into an injection dome for filling a shell of a breast implant with the fluid, in accordance with one embodiment of the present patent application.

Referring to FIG. 7, in one embodiment, an injection dome 268 may be coupled with a proximal end of the tube 206. In one embodiment, the injection dome 268 preferably includes an area 270 that is adapted to receive an injection needle 272. In one embodiment, the area 270 adapted to receive the injection needle 272 may include an injection cover 274. In one embodiment, a distal end of the injection needle 272 may be passed through the injection cover 274 for introducing fluid into the injection dome 268. As the fluid is introduced into the injection dome 268, the fluid preferably passes downstream through the tube 206, through the valve 220 (FIG. 5), and into the inner chamber defined by the shell of the breast implant.

Figure 8:
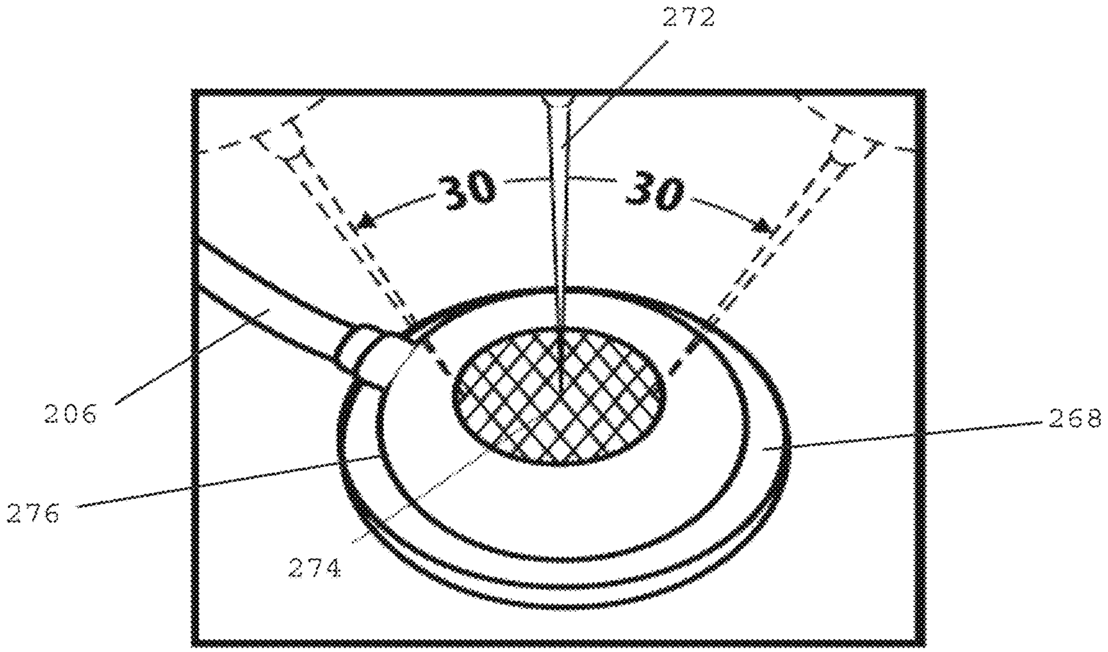
FIG. 8 shows a top perspective view of the injection dome illustrated in FIG. 7 and a range of angles at which the injection needle can be inserted into the injection dome, in accordance with one embodiment of the present patent application.

Referring to FIG. 8, in one embodiment, the distal end of the injection needle 272 is preferably passed through the injection cover 274 provided at the upper end of the injection dome 268. As shown in FIG. 8, in one embodiment, the injection needle 272 preferably forms an angle of no greater than thirty degrees (30°) with a plane defined by the top surface of the injection cover 274 so that the distal end of the injection needle 272 does not pierce a sidewall 276 of the injection dome 268. When the fluid is dispensed inside the injection dome 268, the fluid preferably advances downstream through the tube 206 for expanding the size of the shell of the breast implant.

Figure 9A:
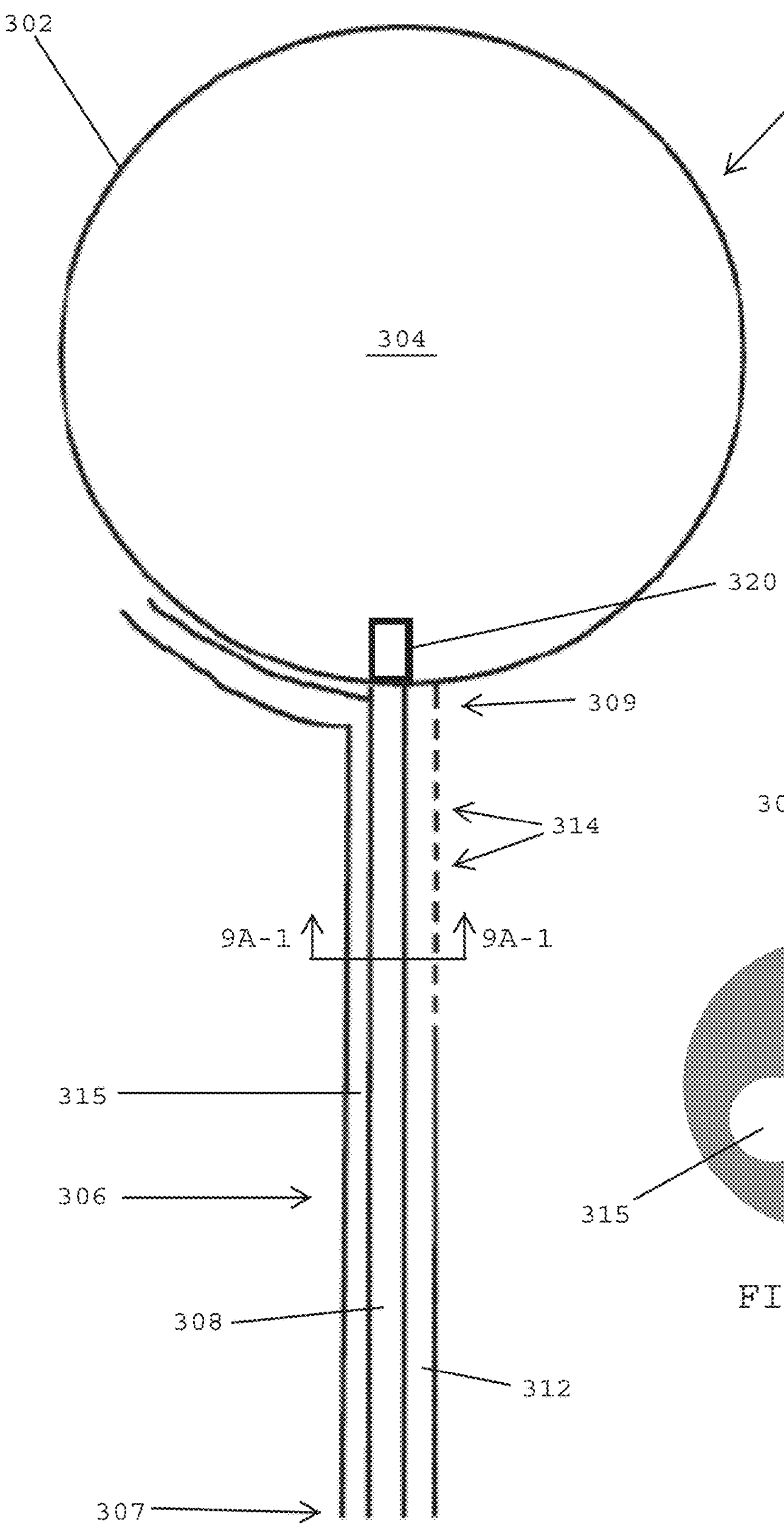
FIG. 9A is a schematic view of a breast implant including a shell and a triple-lumen tube including a first lumen for filling the shell with a fluid, a second lumen for draining fluids that accumulate outside the shell, and a third lumen for infusing fluid into a breast pocket that surrounds the shell, in accordance with one embodiment of the present patent application.
Figures 1, 9A:
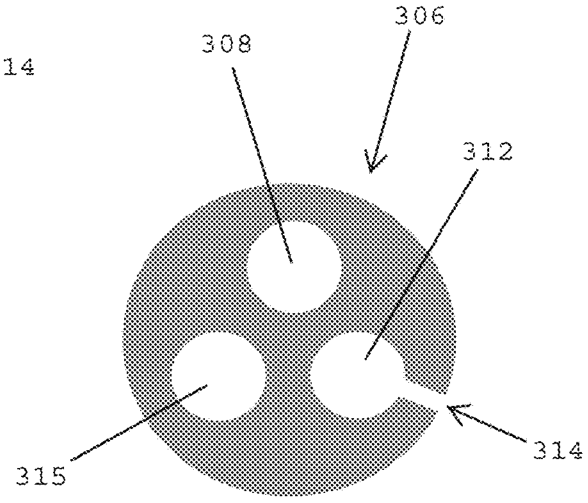
Figure 9B:
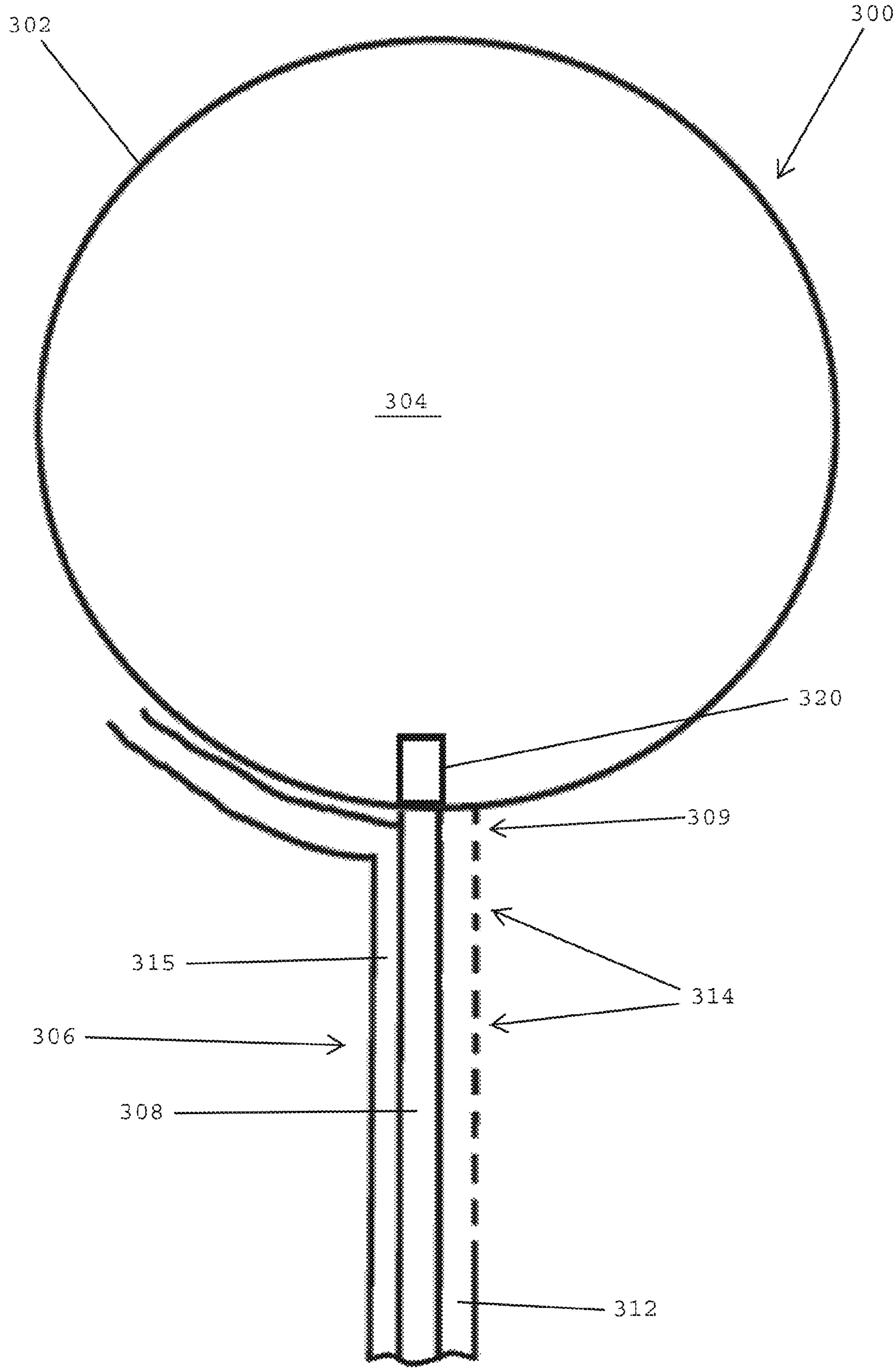
FIG. 9B is a magnified view of the shell and a distal end of the triple-lumen tube shown in FIG. 9A.

Referring to FIGS. 9A and 9B, in one embodiment, a breast implant 300 preferably includes a shell 302 that defines an inner chamber 304 that is configured for being filled with a fluid such as saline for expanding the size of the shell. In one embodiment, the breast implant 300 desirably includes a tube 306 having a proximal end 307 and a distal end 309 that is connected with the shell 302. In one embodiment, the tube 306 is a triple-lumen tube that desirably includes a first lumen 308 (i.e., a fill lumen) that is utilized for introducing a fluid into the inner chamber 304 of the shell 302 for expanding the size of the shell. In one embodiment, the distal end of the first lumen 308 is in communication with a valve 320 that is configured to enable the fluid to pass through the valve (e.g., when the valve is open) and into the inner chamber 304 for filling the shell 302, while preventing the fluid disposed within the inner chamber 304 from leaking from the shell 302.

In one embodiment, the tube 306 desirably includes a second lumen 312 (i.e., a drain lumen) that is utilized for draining fluid (e.g., seroma) that collects around the outer perimeter of the shell 302. In one embodiment, the tube 306 desirably includes a series of lateral openings 314 (e.g., drainage openings) that are in fluid communication with the second lumen 312 for draining the fluid that collects around the shell 302 of the breast implant 300. In one embodiment, the lateral openings 314 may include a series of openings that extend adjacent the distal end 309 of the tube 306. In one embodiment, the series of lateral openings 314, located adjacent the distal end 309 of the tube 306, extend approximately one-third of the length of the tube 306.

In one embodiment, the tube 306 desirably includes a third lumen 315 (i.e., an infusion lumen) that may be utilized for infusing fluid into a breast pocket that surrounds the outer perimeter of the shell 302 of the breast implant 300. In one embodiment, the fluid that is infused into the breast pocket may be a sterile saline or therapeutic solution to enhance healing and recovery. In one embodiment, after the fluid is infused into the breast pocket via the third lumen 315, the infused fluid may be simultaneously or sequentially withdrawn (e.g., suctioned) from the breast pocket via the series of lateral openings 314 that are in fluid communication with the second lumen 312.

In one embodiment, the second and third lumens of a tube may be used interchangeably. For example, in one embodiment, the second lumen may initially be used for draining a fluid that accumulates around the shell of a breast implant and the third lumen may be used for infusing a fluid around the shell of the implant. At a different stage, the second lumen may be used for infusing a fluid around the shell of the breast implant and the third lumen may be used for draining fluids that accumulate around the shell of the breast implant.

Referring to FIG. 9A-1, in one embodiment, the tube 306 preferably includes the first lumen 308 that is utilized for filling the shell of the breast implant, the second lumen 312 that is utilized for draining fluid that collects around the outer perimeter of the shell of the breast implant, and the third lumen 315 that is utilized for infusing fluid into a breast pocket that surrounds the shell 302 of the breast implant 300.

In one embodiment, the tube 306 includes the series of lateral openings 314 that are formed in a sidewall of the tube and that are in fluid communication with the second lumen 312. The series of lateral openings 314 enable the fluid that collects and/or is infused around the outer perimeter of the breast implant to be drawn (e.g., suctioned) into the second lumen 314 for being drained from a patient.

Figure 10A:
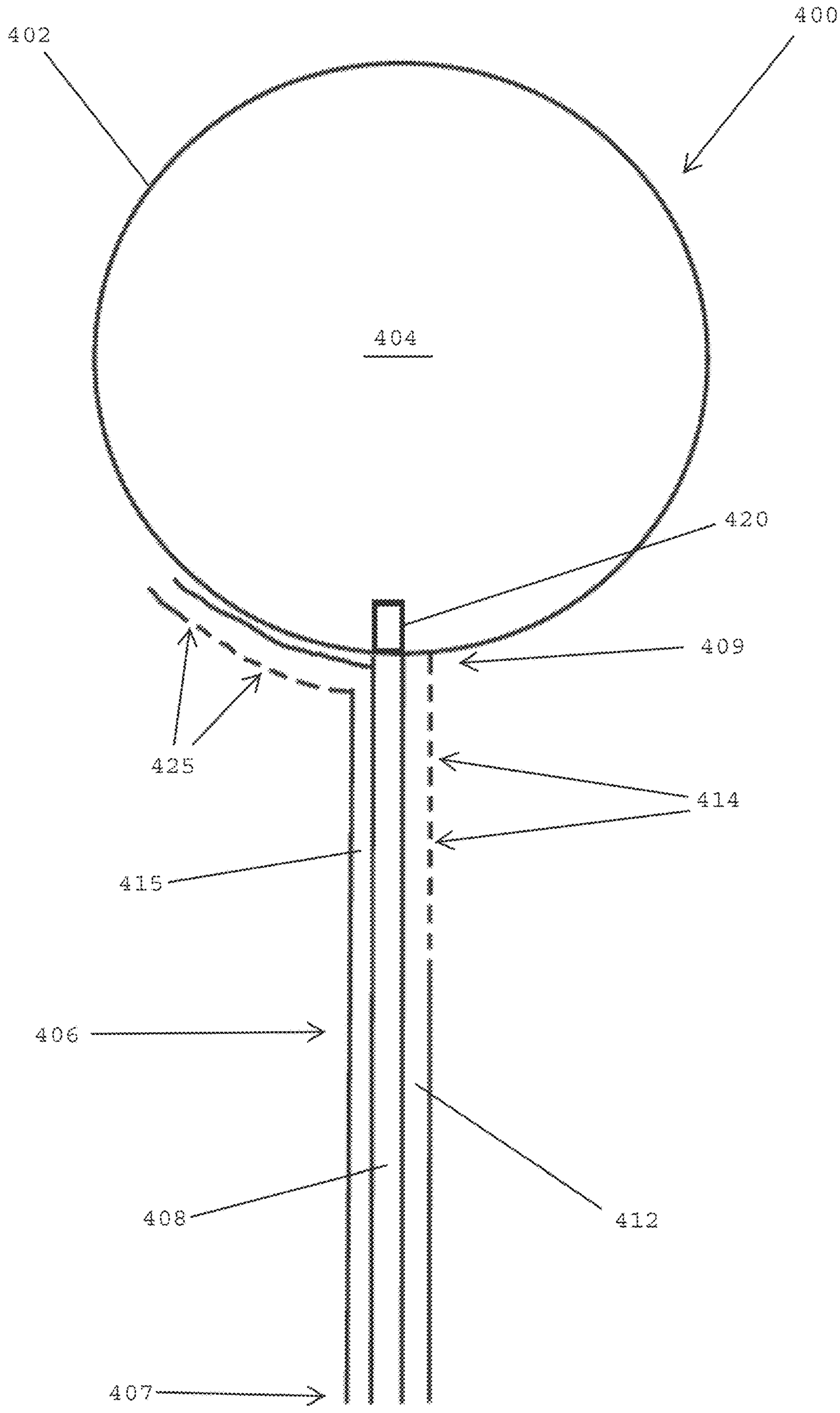
FIG. 10A is a schematic view of a breast implant including a shell and a triple-lumen tube including a first lumen for filling the shell with a fluid, a second lumen for draining fluid that accumulates outside the shell, and a third lumen for infusing fluid into a breast pocket that surrounds the shell, in accordance with one embodiment of the present patent application.
Figure 10B:
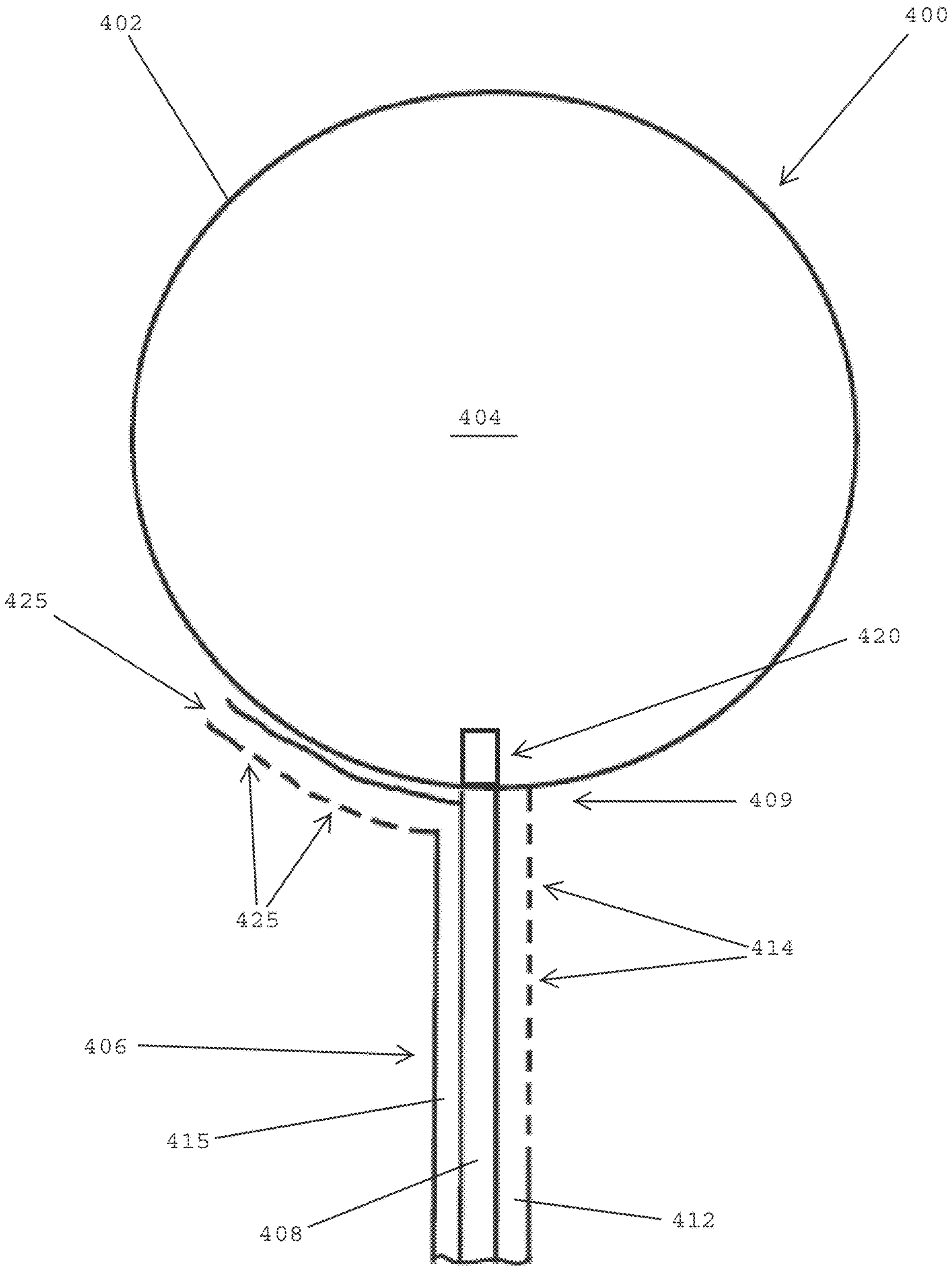
FIG. 10B is a magnified view of the shell and a distal end of the triple-lumen tube shown in FIG. 10A.

Referring to FIGS. 10A and 10B, in one embodiment, a breast implant 400 preferably includes a shell 402 that surrounds an inner chamber 404 that is adapted to receive a fluid (e.g., saline) for expanding the size of the shell 402. In one embodiment, the breast implant 400 preferably includes a valve 420 that is disposed inside the shell 402 for enabling the shell to be filled with a fluid. The valve is normally closed but may be opened for filling the shell with a fluid. The valve desirably prevents fluid disposed within the inner chamber 404 of the shell from inadvertently leaking from the breast implant 400. In one embodiment, the valve 420 enables medical personnel to selectively manipulate the valve for filling the inner chamber 404 of the shell 402 with a fluid (e.g., saline) while preventing any fluid disposed within the shell 402 from leaking from the breast implant 400.

In one embodiment, the breast implant 400 preferably includes an elongated tube 406 having a proximal end 407 and a distal end 409. In one embodiment, the distal end 409 of the tube 406 may be selectively connected with and disconnected from the shell 402 of the breast implant 400. In one embodiment, the elongated tube 406 desirably includes a first lumen 408 that is in fluid communication with the valve 420. The first lumen may be utilized for filling the inner chamber 404 of the shell 402 with a fluid.

In one embodiment, the elongated tube 406 desirably includes a second lumen 412 that may be utilized for draining fluid (e.g., seroma) that collects around the outer perimeter of the shell 402 of the breast implant 400. In one embodiment, the elongated tube 406 desirably includes a series of lateral openings formed in an outer wall thereof that are in fluid communication with the second lumen 412. The lateral openings 414 enable fluid that collects around the shell 402 of the breast implant 400 to be drawn into the second lumen 412 for being drained from a patient.

In one embodiment, the elongated tube 406 desirably includes a third lumen 415 that may be used for infusing fluid and/or a therapeutic solution around the outer perimeter of the shell 402 of the breast implant 400. In one embodiment, the distal end of the elongated tube 406 may include a series of fluid infusing openings 425 that are formed in a sidewall of the elongated tube 406 for infusing a fluid into a breast pocket that surrounds the shell 402 of the breast implant 400. In one embodiment, the series of fluid infusing openings 425 may be in fluid communication with the third lumen 415 so that a fluid directed into the third lumen 415 may be dispensed into a breast pocket via the series of fluid-infusing openings 425 located adjacent the distal end of the third lumen 415. In some embodiments, the lateral openings 414 are located at the lowest point of the implant 400 when the patient is oriented standing or at the lowest point when the patient is oriented laying of their back. In some embodiments, at least some of the fluid infusing openings 425 are distal from the lateral openings 414 and positioned along the shell wall 402.

Figure 11A:
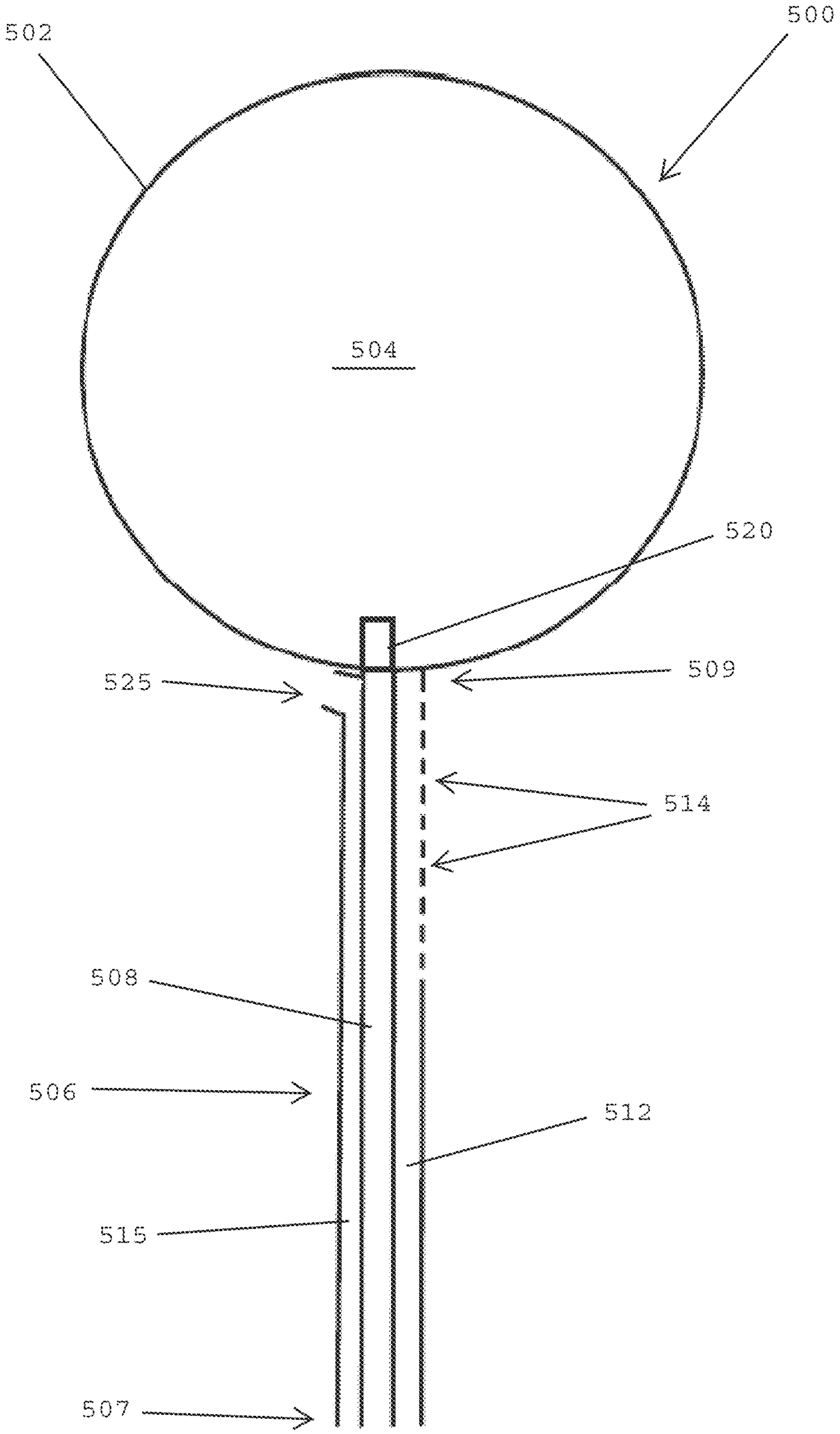
FIG. 11A is a schematic view of a breast implant including a shell and a triple-lumen tube including a first lumen for filling the shell with a fluid, a second lumen for draining fluid that accumulates around the shell, and a third lumen for infusing fluid into a breast pocket that surrounds the shell, in accordance with one embodiment of the present patent application.
Figure 11B:
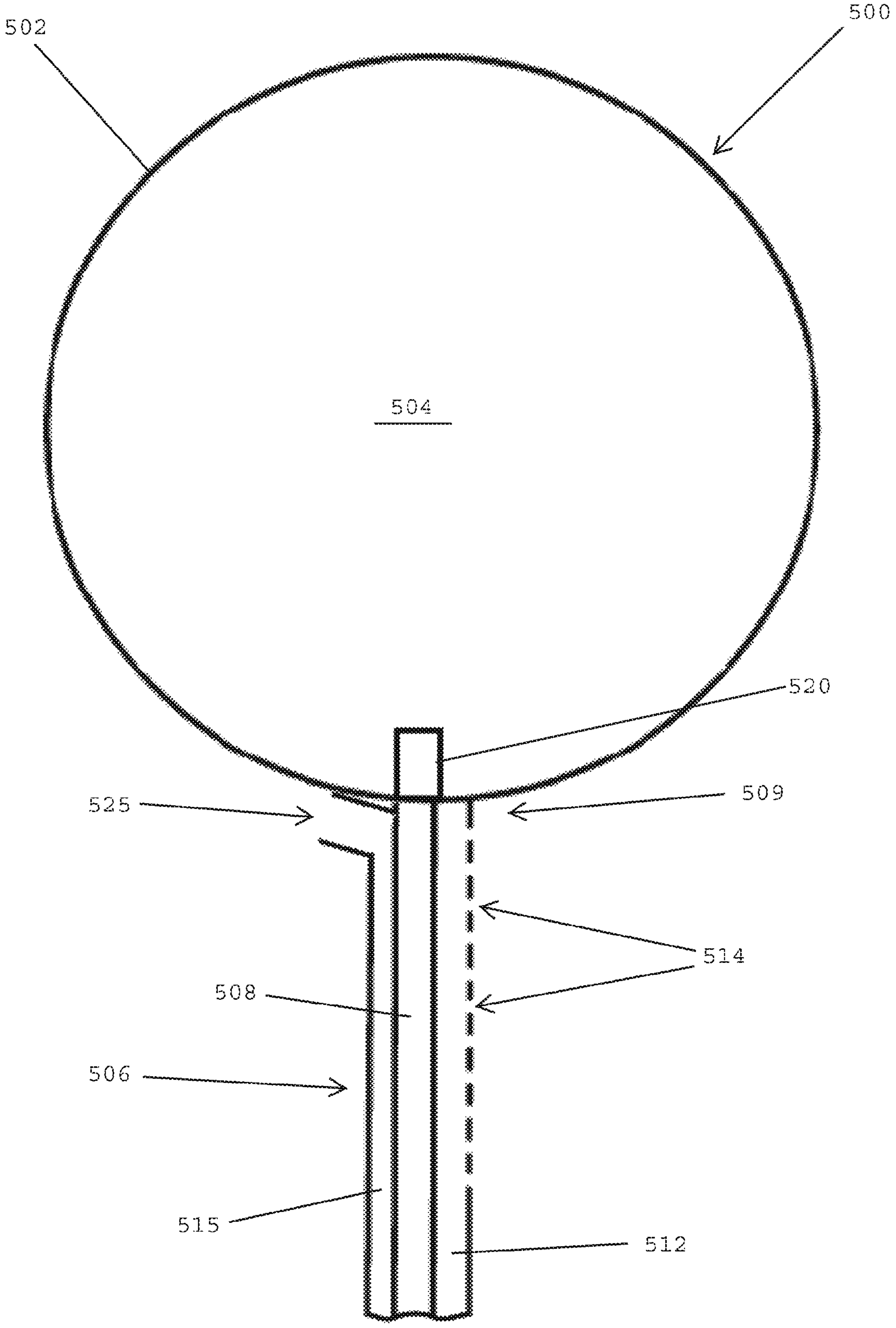
FIG. 11B is a magnified view of the shell and a distal end of the triple-lumen tube shown in FIG. 11A.

Referring to FIGS. 11A and 11B, in one embodiment, a breast implant 500 desirably includes a shell 502 that surrounds an inner chamber 504, which is configured to receive a fluid (e.g., saline) for expanding the size of the shell 502. In one embodiment, the breast implant 500 desirably includes a valve 520 disposed within the inner chamber 504 of the shell 502, which enables fluid to be introduced into the inner chamber 504 for expanding the size of the shell 502, while preventing any fluid within the inner chamber 504 from leaking from the shell 502. The valve is normally dosed, but may be opened for adding and/or removing fluid from the shell.

In one embodiment, the breast implant 500 desirably includes an elongated tube 506 having a proximal end 507 and a distal end 509. The distal end of the elongated tube is preferably configured for being releasably secured to the valve 520 that extends into the inner chamber 504 of the shell 502. In one embodiment, the elongated tube 506 desirably includes a first lumen 508 that may be utilized for delivering a fluid to the inner chamber 504 of the shell 502. In one embodiment, the first lumen 508 is desirably in fluid communication with the valve 520 of the breast implant 500 for adding and/or removing fluid from the shell.

In one embodiment, the elongated tube 506 desirably includes a second lumen 512, which may be utilized for draining fluid that collects around an outer perimeter of the shell 502 of the breast implant 500. In one embodiment, the elongated tube 506 desirably includes a series of lateral openings 514 formed in an outer wall thereof that are in fluid communication with the second lumen 512. In one embodiment, a vacuum may be introduced at a proximal end of the second lumen 512 for drawing fluid that has collected around the shell 502 through the lateral openings 514 and into the second lumen 512 for being drained from a patient.

In one embodiment, the elongated tube 506 desirably includes a third lumen 515 having a distal opening 525, which may be utilized for infusing a fluid (e.g., a therapeutic solution; an antibiotic solution) into a breast pocket that surrounds an outer perimeter of the shell 502 of the breast implant 500. In one embodiment, the fluid may be introduced into the third lumen 515 via an opening at the proximal end 507 of the elongated tube 506. The fluid preferably traverses toward the distal end 509 of the elongated tube 506 for being dispensed from the third lumen 515 via the distal opening 525.

In one embodiment, the dual-lumen or three lumen tubes disclosed herein may be wrapped completely around the outer perimeters of the shells of breast implants for draining fluid that accumulates around the outer perimeters of the shells and/or for infusing fluid around the outer perimeters of the shells.

Figure 12:
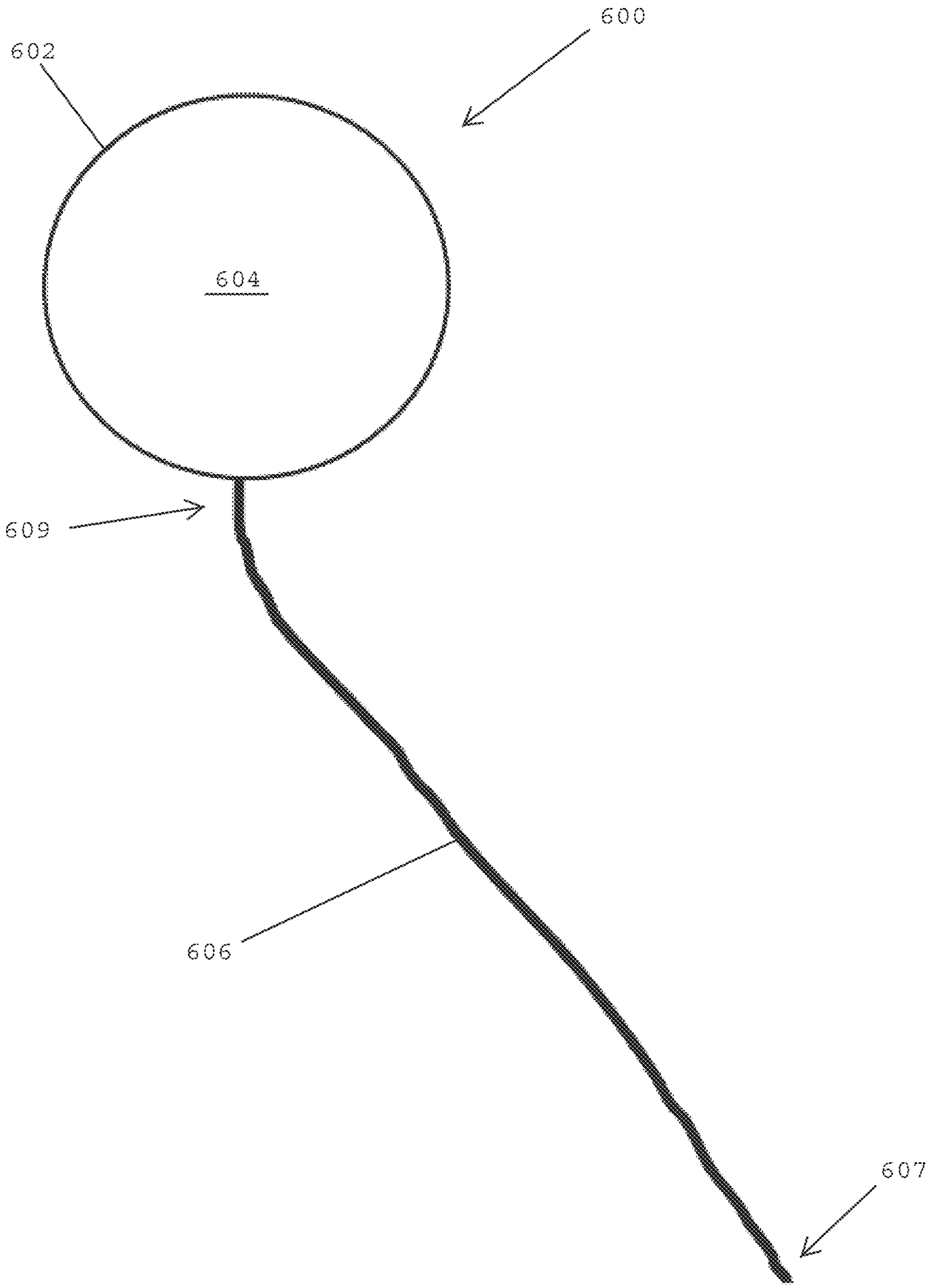
FIG. 12 is a schematic view of a breast implant including a shell and a dual-lumen tube having a first lumen for filling the shell with a fluid and a second lumen for draining fluid that accumulates around the perimeter of the shell, in accordance with one embodiment of the present patent application.
Figure 13:
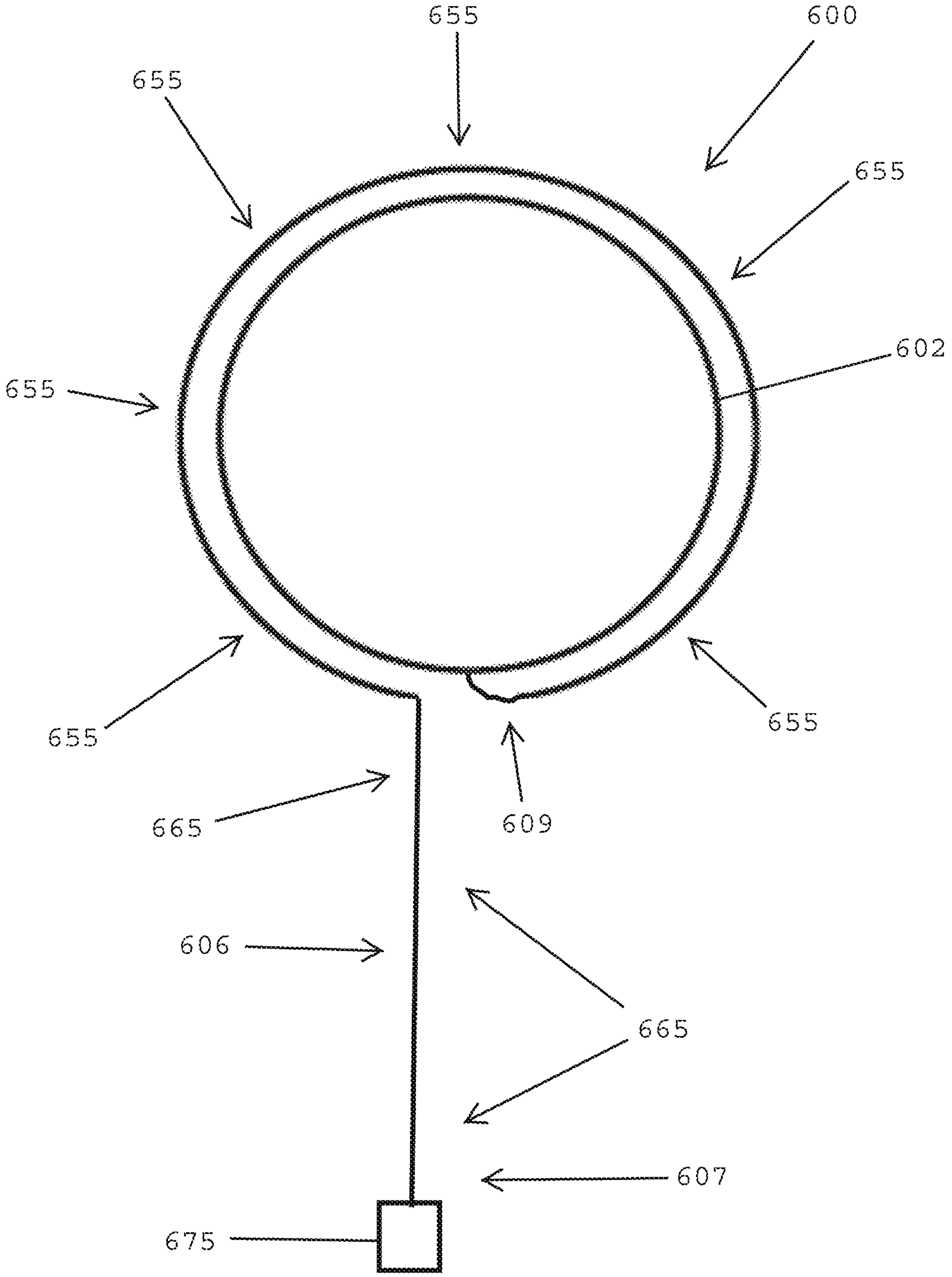
FIG. 13 shows the breast implant of FIG. 12 with a section of the dual-lumen tube wrapped completely around an outer perimeter of the shell of the breast implant for draining fluid from around the outer perimeter of the shell.

Referring to FIGS. 12 and 13, in one embodiment, a breast implant 600 preferably includes a shell 602 that defines an inner chamber 604 that is configured for being filled with a fluid, such as saline.

In one embodiment, the breast implant 600 preferably includes a dual-lumen tube 606, which may be similar to the dual-lumen tube 206 shown and described above in FIGS. 2A and 2B. In one embodiment, the dual-lumen tube 606 preferably has a proximal end 607 and a distal end 609. The distal end 609 of the dual-lumen tube 606 may be inserted into an opening in the shell that is used for filling the shell with a fluid (e.g., saline).

In one embodiment, the dual-lumen tube 606 preferably includes a first lumen that extends between the proximal end 607 and the distal end 609 of the dual-lumen tube 606. The first lumen is preferably configured for introducing a fluid, such as saline, into the inner chamber 604 of the shell 602 for expanding the size of the breast implant 600. The first lumen may also be used for removing fluid from the inner chamber 604 of the shell 602 for reducing the size of the breast implant 600.

In one embodiment, the dual-lumen tube 606 preferably includes a second lumen that is configured for draining fluid (e.g., seroma; bodily fluids) that accumulates around an outer perimeter of the shell 602. In one embodiment, the dual-lumen tube 606 preferably includes a series of lateral openings formed therein that are in fluid communication with the second lumen for enabling bodily fluids that accumulate around the outer perimeter of the shell 602 to be drawn and/or suctioned into the second lumen for being removed from the patient's body.

Referring to FIG. 13, in one embodiment, a section 655 of the dual lumen tube 606 is wrapped around the outer perimeter of the shell 602. The section 655 of the dual-lumen tube 606 that is wrapped around the outer perimeter of the shell may assume a shape (e.g., circular; a ring shape) that matches the shape of the outer perimeter of the shell 602. In one embodiment, the section 655 of the dual-lumen tube 606 that is wrapped around the outer perimeter of the shell preferably includes the series of lateral openings that are configured for draining fluid (e.g., seroma) that accumulates around the outer perimeter of the shell 602 of the breast implant 600. The series of lateral openings that are in fluid communication with the second lumen are desirably implanted inside the patient so that the lateral openings are not exposed to ambient air, which prevents ambient air from being sucked into the second lumen as fluid is being drained from around the perimeter of the shell 602 of the breast implant 600. In one embodiment, the series of lateral openings for draining fluid from around the outer perimeter of the shell 602 of the breast implant 600 may extend up to 90% or more of the total length of the dual-lumen tube 606.

In one embodiment, a second section 665 of the dual-lumen tube 606 that is not wrapped around the outer perimeter of the shell 602 of the breast implant 600 is devoid of the lateral openings. The section 665 that is devoid of the lateral openings may be positioned outside the patient's body.

In one embodiment, the proximal end 607 of the dual-lumen tube 606 may be coupled with an injection dome 675 or a port assembly as disclosed in commonly assigned U.S.

Pat. Nos. 8,349,007 and 11,185,384, the disclosures of which are hereby incorporated by reference herein. The injection dome 675 or port assembly may be implanted inside a patient or may be located outside the patient.

Figure 14:
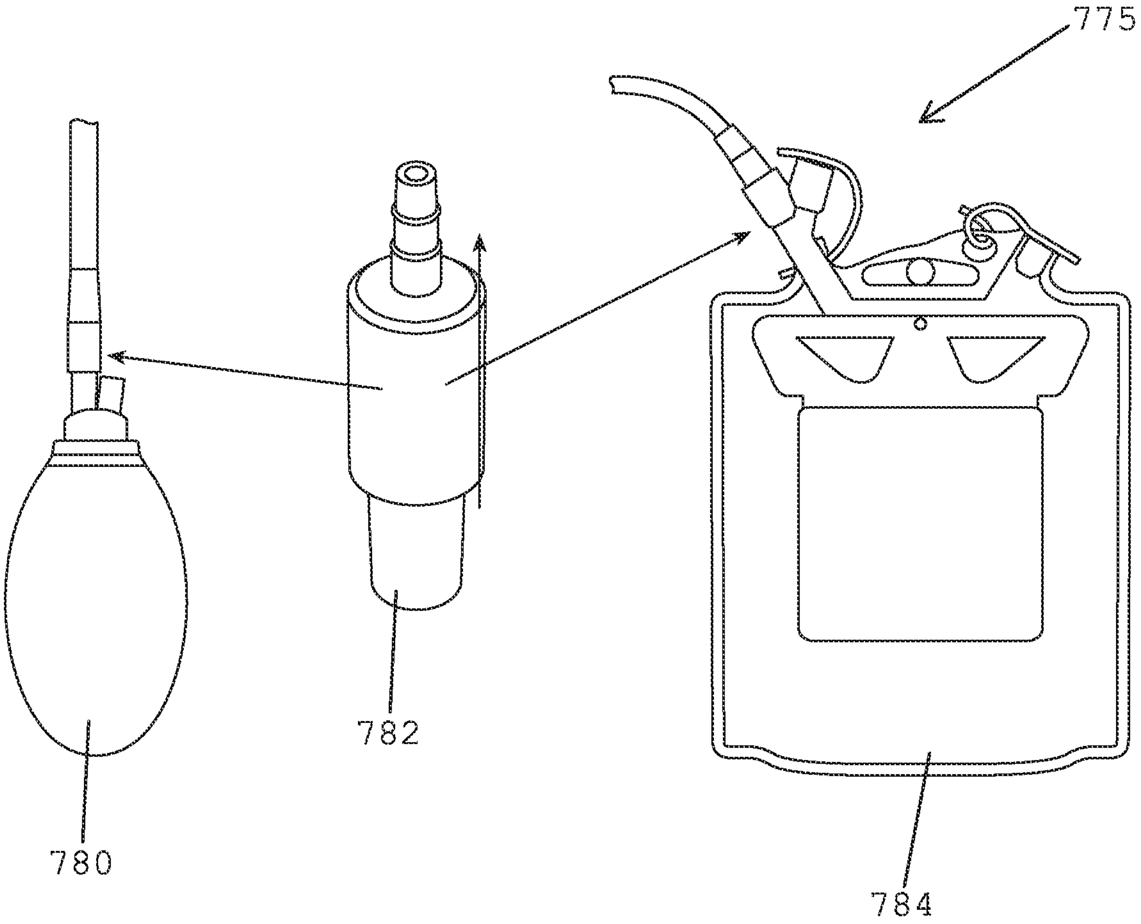
FIG. 14 shows a system for applying vacuum to an end of a wound drain tube for draining fluids from a patient, in accordance with embodiment of the present patent application

Referring to FIG. 14, in one embodiment, a system 775 may be used for creating a vacuum to drain fluid that has accumulated around a breast implant after the breast implant has been implanted inside a patient. The systems may include components that are configured for being coupled with the tubes, injections chambers, and/or injection ports disclosed herein for drawing any fluid that has accumulated around the outsides of the outer shells of the respective breast implants. In one embodiment, the system 775 for generating a vacuum preferably includes a compressible bulb 780. In one embodiment, vacuum may be created using a flexible, compressible reservoir 782 that draws a substantially constant vacuum to permit uniform removal of fluid from a breast pocket via a tube, such as the surgical fluid evacuator system disclosed in U.S. Pat. No. 4,429,693 to Blake et al., the disclosure of which is hereby incorporated by reference herein. In one embodiment, the system 775 may include a metered container 784, which may be used for drawing a vacuum to permit the uniform removal of fluid from a surgical site.

In one or more embodiments, in use, filling the implant with saline may be performed independently of the step of draining the implant via the second lumen. In other embodiments, performing inflating or filling of the implant may occur simultaneously with draining, wherein infusion of saline into the implant provides additional pressure on the tissue pocket and facilitates expelling of the fluids accumulating around the implant within the tissue pocket. In one or more embodiments, in use, the infusion of saline or therapeutic liquids via the third lumen may be performed simultaneously with the draining via the second lumen.

In other embodiments, flushing of the tissue pocket may be performed using different options and/or step.

Option A. Step 1. Infuse liquid into tissue pocket via the third lumen, and thereafter, Step 2. Initiate draining via the second lumen.

Option B. Step 1. Infuse liquid into tissue pocket via the third lumen, and simultaneously perform draining via the second lumen.

Option C. Step 1. Infuse liquid into the tissue pocket via the third lumen, and thereafter, Step 2. Initiate draining via the second lumen while simultaneously inflating the shell via the first lumen.

Option D. Step 1. Deflate the shell by removing a portion of the fill liquid from the shell via the first lumen, and simultaneously or sequentially infuse liquid into the tissue pocket via the third lumen. Step 2. Initiate draining via the second lumen while simultaneously re-inflating the shell by infusing the shell via the first lumen.

In one embodiment, an assembly (e.g., an injection dome; an external port) for filling a shell of breast implant with a fluid (e.g., saline) and/or for draining a fluid (e.g., seroma) that accumulates around the shell of the breast implant may have a first chamber in fluid communication with a first lumen (e.g., the fill lumen) of the tube and a second chamber in fluid communication with a second lumen (e.g., the drain lumen) of the tube.

In one embodiment, the assembly (e.g., an injection dome; an external port) for filling and draining may include a dual chamber injection dome as disclosed in commonly assigned U.S. Pat. No. 8,349,007 to Berg et al., the disclosure of which is hereby incorporated by reference herein.

In one embodiment, an assembly (e.g., an injection dome; an external port) for performing filling, draining and infusion functions may have a first chamber in fluid communication with a first lumen (e.g., the fill lumen) of the tube, a second chamber in fluid communication with a second lumen (e.g., the drain lumen) of the tube, and a third chamber in fluid communication with a third lumen (e.g., an infusion lumen) of the tube.

In one embodiment, the assembly (e.g., an injection dome; an external port) may include one or more of the injection port assemblies disclosed in commonly assigned U.S. Pat. No. 11,185,384 to Feinberg et al., the disclosure of which is hereby incorporated by reference herein. Although the Feinberg '384 patent discloses an integrated injection port assembly, the present patent application may include one or more embodiments whereby the injection port assemblies are external components that are coupled with the shell of the breast implant via one or more tubes including the first, second and/or third lumens. The assembly may include needles (e.g., injection needles; drainage needles, infusion needles) having distal openings and/or side openings as disclosed in various embodiments of the Feinberg '384 patent.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A breast implant comprising:

an implant shell having an inner chamber; and a tube having a proximal end and a distal end, wherein the distal end of said tube is detachably connected with said implant shell;

said tube having a first lumen that extends between the proximal and distal ends thereof, wherein said first lumen is in fluid communication with said inner chamber for adding fluid into said inner chamber to increase the size of said implant shell or for removing fluid from said inner chamber to reduce the size of said implant shell;

said tube having a second lumen and one or more lateral openings that are in fluid communication with said second lumen for draining fluid that collects in tissue surrounding an outer perimeter of said implant shell; and said tube further comprising a third lumen that extends along the length of said tube for infusing a therapeutic fluid into the tissue surrounding the outer perimeter of said implant shell.

2. The breast implant as claimed in claim 1, further comprising:

a fluid inlet opening formed in said implant shell; and a valve disposed within said fluid inlet opening, wherein said valve is normally biased in a closed position.

3. The breast implant as claimed in claim 2, wherein the distal end of said tube is detachably connected with said implant shell via said fluid inlet opening, and wherein when the distal end of said tube is inserted into said fluid inlet opening, the distal end of said tube forces said valve into an open position for providing fluid communication between said first lumen and said inner chamber.

4. The breast implant as claimed in claim 1, wherein said tube is a dual-lumen tube including said first and second lumens extending between the proximal and distal ends of said tube.

5. The breast implant as claimed in claim 1, wherein said one or more lateral openings in fluid communication with said second lumen comprise a series of laterally extending openings that extend along the length of said tube.

6. The breast implant as claimed in claim 5, wherein said tube defines a first length and said series of laterally extending openings define a second length that is less than 90% of the first length.

7. The breast implant as claimed in claim 1, further comprising:

a fill port coupled with a proximal end of said first lumen that is configured for adding fluid into said inner chamber of said implant shell to increase the size of said implant shell;

a drainage port coupled with a proximal end of said second lumen to drain fluid from the tissue surrounding the outer perimeter of said implant shell.

8. The breast implant as claimed in claim 1, further comprising a series of infusion openings formed in said tube that are in fluid communication with said third lumen, wherein said series of infusion openings are configured for infusing the therapeutic fluid into the tissue surrounding the outer perimeter of said implant shell.

9. The breast implant as claimed in claim 8, wherein said series of infusion openings are located adjacent the distal end of said tube and define a length that is less than 50% of the length of said tube.

10. A breast implant comprising:

an elastomeric shell having an inner chamber;

a tube having a proximal end and a distal end;

a fluid inlet opening formed in said elastomeric implant shell; and a valve disposed within said fluid inlet opening, wherein said valve is normally biased in a closed position, said tube including a first lumen that is in fluid communication with said inner chamber for filling said inner chamber with a fluid for expanding said elastomeric shell;

said tube including a second lumen and one or more lateral openings in fluid communication with said second lumen for draining fluid from tissue surrounding an outer perimeter of said shell; and the distal end of said tube being detachably connected with said implant shell via said fluid inlet opening.

11. The breast implant as claimed in claim 10, further comprising:

a third lumen that extends along the length of said tube for infusing a therapeutic fluid into the tissue surrounding the outer perimeter of said elastomeric shell; and a series of laterally extending infusion openings formed in said tube that are in fluid communication with said third lumen, wherein said series of laterally extending infusion openings are configured for infusing the therapeutic fluid into the tissue surrounding the outer perimeter of said elastomeric shell.

12. The breast implant as claimed in claim 11, wherein said series of laterally extending infusion openings define a length that is less than 90% of the length of said tube.

13. A breast implant comprising:

an implant shell having an inner chamber;

a three lumen tube having a proximal end and a distal end, wherein the distal end of said three lumen tube is detachably connected with said implant shell;

said three lumen tube having a first lumen that extends between the proximal and distal ends thereof, wherein said first lumen is in fluid communication with said inner chamber for adding fluid into said inner chamber to increase the size of said implant shell or for removing fluid from said inner chamber to reduce the size of said implant shell;

said three lumen tube having a second lumen and one or more laterally extending drainage openings that are in fluid communication with said second lumen for draining fluid that collects in the tissue surrounding an outer perimeter of said implant shell;

said three lumen tube having a third lumen and one or more laterally extending infusion openings that are in fluid communication with said third lumen for infusing fluid into the tissue surrounding the outer perimeter of said implant shell.

14. The breast implant as claimed in claim 13, further comprising:

a fluid inlet opening formed in said implant shell;

a valve disposed within said fluid inlet opening, wherein said valve is normally biased in a closed position, and wherein said first lumen is in fluid communication with said fluid inlet opening and said inner chamber for filling said inner chamber with a fluid for expanding said implant shell.

15. The breast implant as claimed in claim 14, wherein the distal end of said tube is detachably connected with said implant shell via said fluid inlet opening.

16. The breast implant as claimed in claim 13, wherein said one or more laterally extending drainage openings extend along the length of said tube, and wherein a section of said tube that contains said laterally extending drainage openings is wrapped around an outer perimeter of said implant shell.

17. The breast implant as claimed in claim 13 further comprising:

a fill port coupled with a proximal end of said first lumen that is configured for adding fluid into said inner chamber of said implant shell to increase the size of said implant shell;

a drainage port coupled with a proximal end of said second lumen to drain fluid from the tissue surrounding the outer perimeter said implant shell;

an infusion port coupled with a proximal end of said third lumen to infuse fluid into the tissue surrounding the outer perimeter said implant shell.

* * * * *